United States Patent
Popp et al.

(10) Patent No.: US 10,575,998 B2
(45) Date of Patent: Mar. 3, 2020

(54) FOLDED DISPOSABLE ABSORBENT GARMENT AND A PACKAGE OF SUCH GARMENTS

(71) Applicant: KIMBERLY-CLARK WORLDWIDE, INC., Neenah, WI (US)

(72) Inventors: Robert Lee Popp, Hortonville, WI (US); Marcille Faye Ruman, Oshkosh, WI (US); Kathleen Irene Bennett, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 555 days.

(21) Appl. No.: 15/353,081

(22) Filed: Nov. 16, 2016

(65) Prior Publication Data

US 2017/0065467 A1   Mar. 9, 2017

Related U.S. Application Data

(63) Continuation of application No. 14/049,589, filed on Oct. 9, 2013, now Pat. No. 9,539,153, which is a
(Continued)

(51) Int. Cl.
  *A61F 13/551*  (2006.01)
  *A61F 13/56*   (2006.01)
  (Continued)

(52) U.S. Cl.
  CPC .. *A61F 13/55115* (2013.01); *A61F 13/49009* (2013.01); *A61F 13/49015* (2013.01);
  (Continued)

(58) Field of Classification Search
  CPC ................ A61F 13/55115; A61F 13/49001
  (Continued)

(56) References Cited

U.S. PATENT DOCUMENTS 3,338,992 A   8/1967   Kinney
3,341,394 A   9/1967   Kinney
(Continued)

FOREIGN PATENT DOCUMENTS

CA   2281716 A1   8/1998
CN   1234216 A    11/1999
(Continued)

OTHER PUBLICATIONS

Translations of JP 2000024030A and 20000240029A provided by Applicant.
(Continued)

*Primary Examiner* — Susan S Su
(74) *Attorney, Agent, or Firm* — Armstrong Teasdale LLP

(57) ABSTRACT

A folded disposable absorbent garment has an absorbent chassis, a pair of front side panels extending from a front region of the absorbent chassis, and a pair of back side panels extending from a back region of the absorbent chassis. Each of the front side panels has a first fastening component and each of the back side panels has a second fastening component. Each of the second fastening components is releasably attached to a respective one of the first fastening components to define a pair of refastenable seams. The front side panels and the back side panels are folded such that each of the refastenable seams overlies an outer surface of one of the front region and the back region of the absorbent chassis in a plane generally parallel to the front and back regions of the absorbent chassis.

9 Claims, 14 Drawing Sheets

Related U.S. Application Data continuation of application No. 13/724,165, filed on Dec. 21, 2012, now Pat. No. 8,632,515, which is a continuation of application No. 12/102,680, filed on Apr. 14, 2008, now Pat. No. 8,372,052, which is a continuation of application No. 09/799,814, filed on Mar. 5, 2001, now abandoned.

(51) Int. Cl.
*A61F 13/49* (2006.01)
*A61F 13/62* (2006.01)
*A61F 13/84* (2006.01)
*B65D 85/62* (2006.01)

(52) U.S. Cl.
CPC .......... *A61F 13/565* (2013.01); *A61F 13/622* (2013.01); *A61F 13/84* (2013.01); *B65D 85/62* (2013.01); *A61F 2013/8497* (2013.01)

(58) Field of Classification Search
USPC .................................................. 604/358–391
See application file for complete search history.

(56) References Cited

U.S. PATENT DOCUMENTS

| | | | |
|---|---|---|---|
| 3,502,538 | A | 3/1970 | Petersen |
| 3,502,763 | A | 3/1970 | Hartmann |
| 3,542,615 | A | 11/1970 | Dobo et al. |
| 3,692,618 | A | 9/1972 | Dorschner et al. |
| 3,802,817 | A | 4/1974 | Matsuki et al. |
| 3,849,241 | A | 11/1974 | Butin et al. |
| 3,981,763 | A | 9/1976 | Brocklehurst |
| 4,050,462 | A | 9/1977 | Woon et al. |
| 4,205,679 | A | 6/1980 | Repke et al. |
| 4,326,528 | A | 4/1982 | Ryan et al. |
| 4,340,563 | A | 7/1982 | Appel et al. |
| 4,581,772 | A | 4/1986 | Smith |
| 4,585,448 | A | 4/1986 | Enloe |
| 4,610,680 | A | 9/1986 | LaFleur |
| 4,615,695 | A | 10/1986 | Cooper |
| 4,663,220 | A | 5/1987 | Wisneski et al. |
| 4,704,116 | A | 10/1987 | Enloe |
| 4,802,884 | A | 2/1989 | Froidh et al. |
| 4,895,569 | A | 1/1990 | Wilson et al. |
| 4,909,804 | A | 3/1990 | Douglas, Sr. |
| 4,940,464 | A | 7/1990 | Van Gompel et al. |
| 5,037,417 | A | 8/1991 | Ternstrom et al. |
| 5,046,272 | A | 9/1991 | Vogt et al. |
| 5,104,116 | A | 4/1992 | Pohjola |
| 5,151,092 | A | 9/1992 | Buell et al. |
| 5,224,405 | A | 7/1993 | Pohjola |
| 5,226,992 | A | 7/1993 | Morman |
| 5,577,540 | A | 11/1996 | Sageser |
| 5,624,425 | A | 4/1997 | Gray et al. |
| 5,779,831 | A | 7/1998 | Schmitz |
| 5,855,574 | A | 1/1999 | Kling et al. |
| 5,971,153 | A | 10/1999 | Bauer et al. |
| 6,050,984 | A | 4/2000 | Fujioka et al. |
| 6,113,717 | A | 9/2000 | Vogt et al. |
| 6,210,388 | B1 | 4/2001 | Widlund et al. |
| 6,287,287 | B1 | 9/2001 | Elsberg |
| 6,444,064 | B1 | 9/2002 | Henry et al. |
| 6,461,344 | B1 | 10/2002 | Widlund et al. |
| 6,478,785 | B1 | 11/2002 | Ashton et al. |
| 6,491,676 | B1 | 12/2002 | Suzuki et al. |
| 7,575,573 | B1 | 8/2009 | Roe et al. |
| 2002/0123730 | A1 | 9/2002 | Popp et al. |
| 2003/0036739 | A1 | 2/2003 | Christoffel et al. |
| 2003/0062113 | A1 | 4/2003 | Van Experen et al. |
| 2003/0062121 | A1 | 4/2003 | Franklin et al. |
| 2005/0027271 | A1 | 2/2005 | Popp et al. |
| 2007/0032770 | A1 | 2/2007 | LeVon et al. |
| 2007/0049890 | A1 | 3/2007 | Popp et al. |

FOREIGN PATENT DOCUMENTS

| | | |
|---|---|---|
| EP | 0217032 A2 | 4/1987 |
| GB | 2245149 A | 1/1992 |
| JP | 3021190 U | 2/1996 |
| JP | 10095481 A | 4/1998 |
| JP | 11113956 A | 4/1999 |
| JP | 2000024029 A | 1/2000 |
| JP | 2000024030 A | 1/2000 |
| JP | 2000024031 A | 1/2000 |
| WO | 9317648 A1 | 9/1993 |
| WO | 9527461 A1 | 10/1995 |
| WO | 9527462 A1 | 10/1995 |
| WO | 9749618 A1 | 12/1997 |
| WO | 0035398 A1 | 6/2000 |
| WO | 0037009 A2 | 6/2000 |
| WO | 2004112518 | 12/2004 |
| WO | 2007123445 | 11/2007 |

OTHER PUBLICATIONS

European Office action for EP 02709388.9 dated Jun. 29, 2010.
Final Written Decision in *First Quality Baby Products, LLC* v. *Kimberly-Clark Worldwide, Inc.*, Case IPR2014-00169, U.S. Pat. No. 8,579,876, May 28, 2015, 33 pages.
Petition for Inter Partes Review of Claims 1-14 and 23-37 of U.S. Pat. No. 8,579,876, *First Quality Baby Products, LLC* v. *Kimberly-Clark Worldwide, Inc.*, Case IPR2016-00168, Nov. 6, 2015, 68 pages.
Exhibit 1002 of Petition for Inter Partes Review of Claims 1-14 and 23-37 of U.S. Pat. No. 8,579,876, Expert Declaration of Daniel D. Gardner in Support of Petition for Inter Partes Review of Claims 1-14 and 23-37 of U.S. Pat. No. 8,579,876, Nov. 6, 2015, 68 pages.
Exhibit 1017 of Petition for Inter Partes Review of Claims 1-14 and 23-37 of U.S. Pat. No. 8,579,876, Excerpts from the Transcripts of of Video Examination of Kent A. Franklin, *First Quality Baby Products, LLC* v. *Kimberly-Clark Norldwide, Inc.*, Case IPR2014-00169 U.S. Pat. No. 8,579,876 B2, Oct. 28, 2014, 16 pages.
Exhibit 1018 of Petition for Inter Partes Review of Claims 1-14 and 23-37 of U.S. Pat. No. 8,579,876, Excerpts from the Declaration of Kent A. Franklin, Case IIPR2014-00169, Sep. 10, 2014, 4 pages.
Exhibit 1016 of Petition for Inter Partes Review of Claims 1-14 and 23-37 of U.S. Pat. No. 8,579,876, Excerpts from the Preliminary Patent Owner's Statement, *First Quality Baby Products, LLC* v. *Kimberly-Clark Worldwide, Inc.*, Case PR2014-00169 U.S. Pat. No. 8,579,876 B2, Mar. 5, 2014, 5 pages.
Exhibit 1008 of Petition for Inter Partes Review of Claims 1-14 and 23-37 of U.S. Pat. No. 8,579,876, Excerpts from the Petition for Inter Partes Review of U.S. Pat. No. 8,579,876, Nov. 19, 2013, 4 pages.
Pull-Ups Training Pants with Easy Open Sides Help Make Potty Training Easier, Kimberly-Clark, May 27, 2003, 1 page.
Transcripts of Video Examination of William Lynch, *Kimberly-Clark Worldwide, Inc. and Kimberly-Clark Global Sales, LLC* vs. *First Quality Baby Products, LLC and First Quality Retail Services, LLC*, Civil Action No. 09-C-916 in the United States District Court Eastern District of Wisconsin Green Bay Division, May 10, 2011, pp. 96-98.
Exhibit 47 of the Video Examination of William Lynch, *Kimberly-Clark Worldwide, Inc. and Kimberly-Clark Global Sales LLC* vs. *First Quality Baby Products, LLC and First Quality Retail Services, LLC*, Civil Action No. 09-C-916 in the United States District Court Eastern District of Wisconsin Green Bay Division, May 10, 2011, 1 page.
Expert Report of John Blevins on the Invalidity of U.S. Pat. No. 8,747,379, *Kimberly-Clark Worldwide, Inc. and Kimberly-Clark Global Sales, LLC* vs. *First Quality Baby Products, LLC and First Quality Retail Services, LLC, and First Quality Consumer Products, LLC*, Case No. 14-CV-1466 in the United States District Court Eastern District of Wisconsin Green Bay Division, May 1, 2015, 280 pages.
Decision—Institution of Inter Partes Review of U.S. Pat. No. 8,579,876, *First Quality Baby Products, LLC* v. *Kimberly-Clark Worldwide, Inc.*, Case IPR2016-00168, May 19, 2016, 31 pages.

FOLDED DISPOSABLE ABSORBENT GARMENT AND A PACKAGE OF SUCH GARMENTS

CROSS REFERENCE TO RELATED APPLICATIONS

This application is a continuation of U.S. patent application Ser. No. 14/049,589, filed Oct. 9, 2013, which is a continuation of U.S. patent application Ser. No. 13/724,165 (issued as U.S. Pat. No. 8,632,515), filed Dec. 21, 2012, which is a continuation of U.S. patent application Ser. No. 12/102,680, filed Apr. 14, 2008 (issued as U.S. Pat. No. 8,372,052), which is a continuation of U.S. patent application Ser. No. 09/799,814, filed Mar. 5, 2001 (now abandoned). The entirety of each of these applications is hereby incorporated by reference.

FIELD OF THE INVENTION

This invention is directed to pant-like garments having refastenable, pre-fastened side seams tucked in a particular position to minimize fastener pop-opens.

BACKGROUND OF THE INVENTION

Pant-like absorbent garments, such as adult incontinence wear, infant and children's diapers, swim wear and training pants, typically have adhesive or mechanical fasteners on the sides for donning and removal, or else rely on a stretchable waist opening and leg openings to slide on and off the wearer. Absorbent garments that slide on and off a wearer can be messy after use. Furthermore, in order to remove such absorbent garments, the wearer's clothing covering the absorbent garments, such as pants, must generally be completely removed. Checking the status of the wearer's absorbent garment contents can be just as cumbersome as changing the absorbent garment.

Refastenable seams including mechanical fasteners, such as, for example, hook and loop fasteners, have been found to be particularly beneficial when used in conjunction with pant-like absorbent garments. Refastenable seams allow for the garment to be easily applied and removed, as well as periodically opened to check for exudates and closed if no exudates are found. Absorbent garments having elastic side panels or other non-refastenable side panels can have the side panels tucked into the center of the product for packaging purposes. Absorbent garments having refastenable side seams, on the other hand, can be prone to poor fastener performance if the side panels are tucked into the product in such a way as to cause creasing of a resilient fastening component.

When the refastenable side seam includes a resilient fastening component such as a hook component, these creases can deaden the hooks, thereby reducing the engageable area. As a result, a creased fastener tends to possess lower peel and/or shear values than uncreased fasteners. Products with severe and/or multiple fastener creases tend to be most apt to pop open during application and wear. Fastener creases appear to be more of an issue for hook components than for loop components due to the possibility of permanent deformation of hook material compared to the relative flexibility of loop material. A major cause of these performance-impairing creases is believed to be attributable to the orientation of the panel bearing the resilient fastening component after tucking of the panel and during product compression for packaging.

There is a need or desire for a tucked fastener in a pant-like, absorbent garment having pre-fastened, refastenable side seams, positioned such that the tucked fastener does not interfere with fastener performance.

SUMMARY OF THE INVENTION

The present invention is directed to packaged garments having tucked refastenable seams. The refastenable seams can extend from a waist opening to each of two leg openings on opposing sides of the pant-like garment and each seam includes at least one resilient fastening component, such as a hook component of a hook and loop fastener. Prior to packaging the garment, the refastenable seams are pre-fastened and tucked into the garment such that the resilient fastening components lie flat in a plane parallel to the planes in which front and back waist portions of the garment lie. Thus, when the garment is compressed and packaged, the resilient fastening components remain flat and do not become creased or crushed.

Various embodiments of the present invention include garments folded into a differential tucked position, a differential undertucked position, an offset tucked position, and an overlapped tucked position. Each of these orientations results in the refastenable seams being tucked between a front region and a back region of the tucked garment. Alternatively, the garment can be folded such that the refastenable seams are tucked outside of the garment chassis.

The orientation of the refastenable seams of the present invention prevents fastener creases from occurring, thus it preserves the available fastener seam strength and makes fasteners, such as hook and loop fasteners, less likely to disengage during product application and wear.

With the foregoing in mind, it is a feature and advantage of the invention to provide a refastenable seam orientation on a garment packaged in a tucked position that does not impair fastener performance.

In one aspect, a folded disposable absorbent garment generally comprises a chassis including longitudinal ends, transverse sides, a front region, a back region, a crotch region extending between and interconnecting the front and back regions, a pair of front side panels, and a pair of back side panels. One of the front side panels is attached to and extends from one transverse side in the front region and the other front side panel is attached to and extends from the other transverse side in the front region. One of the back side panels is attached to and extends from one transverse side in the back region and the other back side panel is attached to and extends from the other transverse side in the back region. First and second refastenable side seams join one of the front side panels to one of the back side panels. The side seams include at least one resilient fastening component. Each of the back side panels and each of the front side panels are folded such that each of the refastenable side seams overlies one of the front region and the back region of the chassis and lies in a plane generally parallel to a plane in which the front and back regions lie.

In another aspect, a package generally comprises a flexible packaging bag defining an interior space and a plurality of disposable absorbent garments disposed within the interior space of the bag. Each of the disposable absorbent garments comprises an absorbent chassis defining a front region, a back region, a crotch region extending between and interconnecting the front and back regions, an inner surface, and an outer surface opposite the inner surface. The crotch region has a fold therein such that the inner surface in the front region generally overlies the inner surface in the back region. A pair of front side panels extends from the front region of the absorbent chassis. Each of the front side panels comprises a first fastening component. A pair of back side panels extends from the back region of the absorbent chassis. Each of the back side panels comprises a second fastening component. Each of the second fastening components is releasably attached to a respective one of the first fastening components to define a pair of refastenable seams. The front side panels and the back side panels are folded such that each of the refastenable seams overlies the outer surface of one of the front region and the back region of the absorbent chassis in a plane generally parallel to the front and back regions of the absorbent chassis. The plurality of disposable absorbent garments are stacked within the interior space of the bag such that the refastenable seams of at least some of the disposable absorbent garments are disposed between the absorbent chassis of adjacent disposable absorbent garments.

In yet another aspect, a pre-fastened, folded training pant generally comprises an absorbent chassis defining a front region, a back region, and a crotch region interconnecting the front and back regions. The crotch region has a fold therein generally about the transverse axis such that the front region and the back region lie in parallel planes. The absorbent chassis comprises an outer cover, a bodyside liner, and an absorbent assembly located between the outer cover and the bodyside liner. A pair of transversely opposed front side panels are attached to the front region of the absorbent chassis. Each of the front side panels are non-elastic and have a hook fastener component attached thereto. A pair of transversely opposed back side panels are attached to the back region of the absorbent chassis. Each of the back side panels are elastic and define at least in part a loop fastener component. Each of the hook fastener components is releasably attached to a respective loop fastener component to define a pair of refastenable seams. Each of the back side panels are folded twice and each of the front side panels are folded once such that each of the refastenable side seams overlies the back region of the chassis and lie in a plane generally parallel to the plane in which the front and back regions lie.

In still another aspect, a folded disposable absorbent garment generally comprises an absorbent chassis defining a front region, a back region, a crotch region extending between and interconnecting the front and back regions, an inner surface, and an outer surface opposite the inner surface. The crotch region has a fold therein such that the inner surface in the front region is in face-to-face relationship with the inner surface in the back region. A pair of front side panels extends from the front region of the absorbent chassis and a pair of back side panels extends from the back region of the absorbent chassis. Each of the front side panels comprises a first fastening component and each of the back side panels comprises a second fastening component. Each of the second fastening components are releasably attached to a respective one of the first fastening components to define a pair of refastenable seams. The front side panels and the back side panels are folded such that each of the refastenable seams overlies the outer surface of one of the front region and the back region of the absorbent chassis in a plane generally parallel to the front and back regions of the absorbent chassis.

In still yet another aspect, a folded disposable absorbent garment generally comprises an absorbent chassis defining a front region, a back region, a crotch region extending between and interconnecting the front and back regions, an inner surface, an outer surface opposite the inner surface, a longitudinal axis, and a transverse axis. The crotch region has a fold therein generally about the transverse axis such that the inner surface in the front region is in face-to-face relationship with the inner surface in the back region. A pair of front side panels extends from the front region of the absorbent chassis and a pair of back side panels extends from the back region of the absorbent chassis. Each of the back side panels at least in part defines a loop fastening component. A hook fastening component is secured to each of the front side panels. Each of the back side panels have a first fold for positioning each of the back side panels in face-to-face relationship with the outer surface of the back region of the absorbent chassis and a second fold spaced from the first fold for facing a portion of the back side panel away from the outer surface of the back region of the absorbent chassis. Each of the front side panels have a fold for positioning each of front side panels in face-to-face relationship with one of the back side panels such that each of the hook fastening component is releasably attached with one of the loop fastening components to define a pair of refastenable seams.

DEFINITIONS

Figure 1:
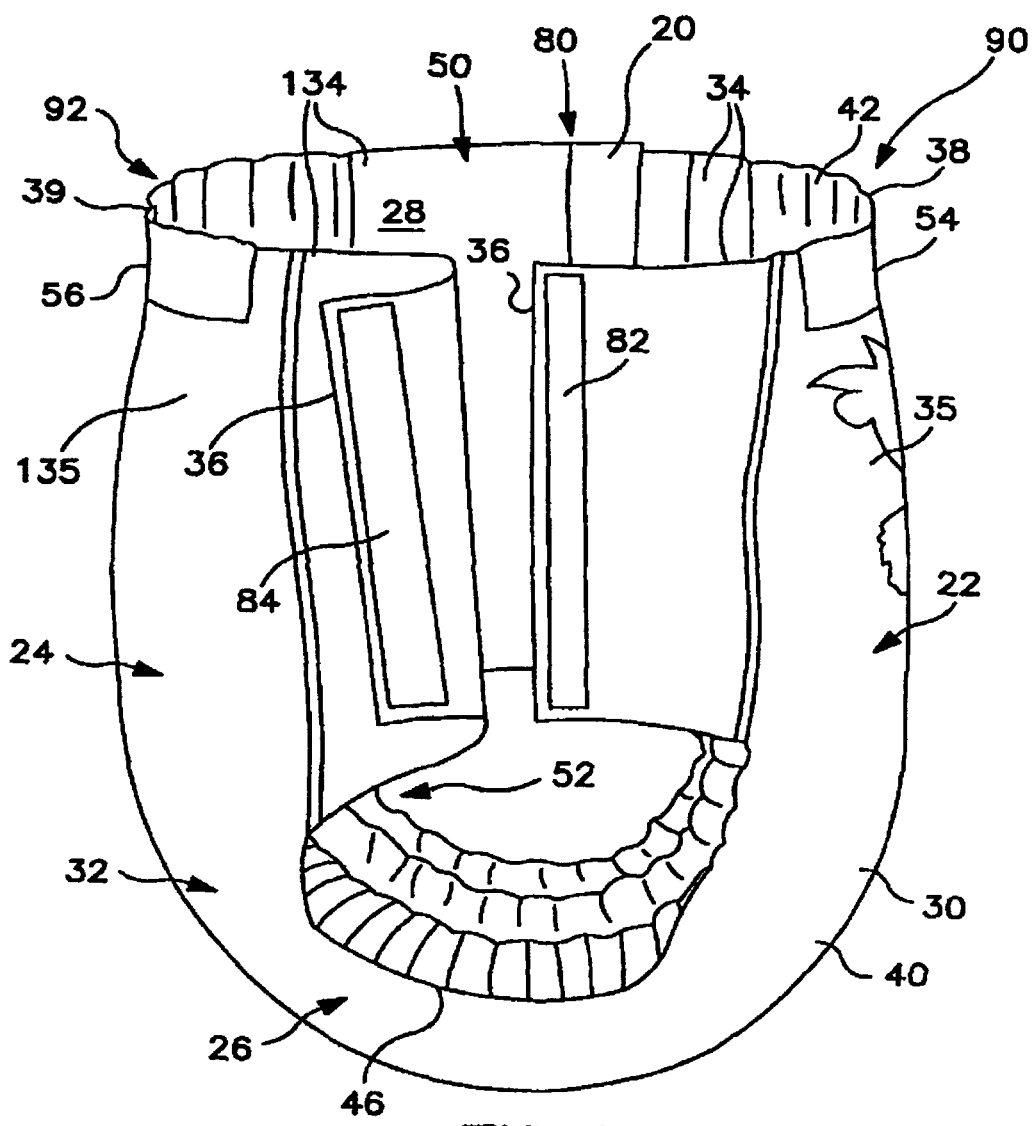
FIG. 1 is a perspective view of an absorbent garment having refastenable side seams.

Within the context of this specification, each term or phrase below will include the following meaning or meanings.

"Attached" refers to the joining, adhering, connecting, bonding, or the like, of at least two elements. Two elements will be considered to be attached to one another when they are attached directly to one another or indirectly to one another, such as when each is directly connected to intermediate elements.

"Bonded" refers to the joining, adhering, connecting, attaching, or the like, of at least two elements. Two elements will be considered to be bonded together when they are bonded directly to one another or indirectly to one another, such as when each is directly bonded to intermediate elements.

"Differential tucked" refers to a folded position of a garment wherein extraneous portions of the garment are closely folded against or between the main body of the garment.

"Differential undertucked" refers to a folded position of a garment wherein at least one extraneous portion of the garment is closely folded against or between the main body of the garment, and at least a second extraneous portion of the garment is loosely folded such that the second extraneous portion is only partially positioned against or between the main body of the garment.

"Elastomeric" and "elastic" refer to that property of a material or composite by virtue of which it tends to recover its original size and shape after removal of a force causing a deformation. It is generally preferred that the elastomeric material or composite be capable of being elongated by at least 50 percent, more preferably by at least 300 percent, of its relaxed length and recover, upon release of an applied force, at least 50 percent of its elongation.

"Film" refers to a thermoplastic film made using a film extrusion process, such as a cast film or blown film extrusion process. The term includes apertured films, slit films, and other porous films which constitute liquid transfer films, as well as films which do not transfer liquid.

"Hydrophilic" describes fibers or the surfaces of fibers which are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials or blends of fiber materials can be provided by a Cahn SFA-222 Surface Force Analyzer System, or a substantially equivalent system. When measured with this system, fibers having contact angles less than 90 are designated "wettable" or hydrophilic, while fibers having contact angles greater than 90 are designated "nonwettable" or hydrophobic.

"Layer" when used in the singular can have the dual meaning of a single element or a plurality of elements.

"Liquid impermeable," when used in describing a layer or multi-layer laminate, means that a liquid, such as urine, will not pass through the layer or laminate, under ordinary use conditions, in a direction generally perpendicular to the plane of the layer or laminate at the point of liquid contact. "Liquid permeable material" or "liquid water-permeable material" refers to a material present in one or more layers, such as a film, nonwoven fabric, or open-celled foam, which is porous, and which is water permeable due to the flow of water and other aqueous liquids through the pores. The pores in the film or foam, or spaces between fibers or filaments in a nonwoven web, are large enough and frequent enough to permit leakage and flow of liquid water through the material.

Figure 2:
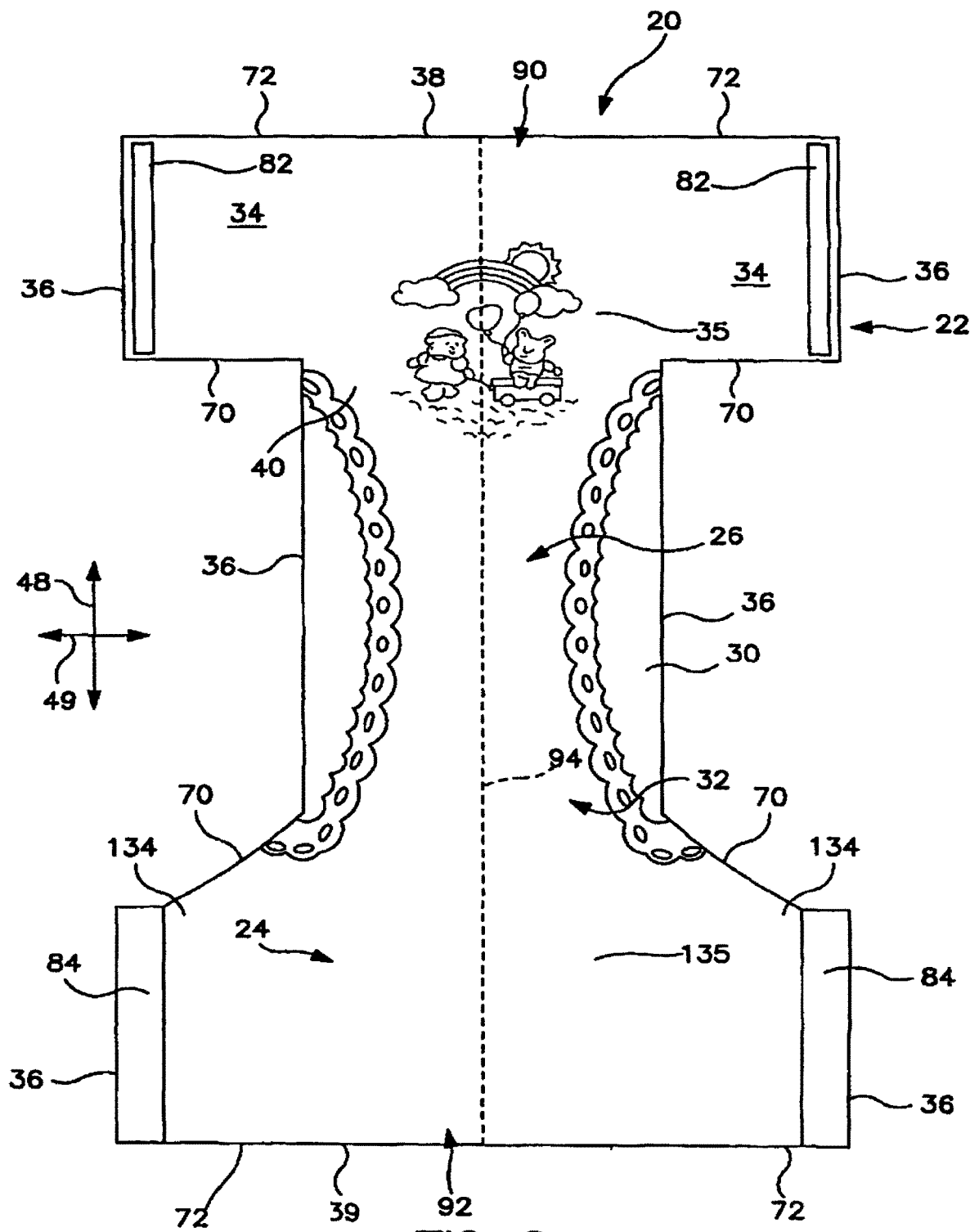
FIG. 2 is a plan view of an absorbent garment in a stretched flat state showing the surface of the garment that faces away from the wearer when the garment is worn.
Figure 3:
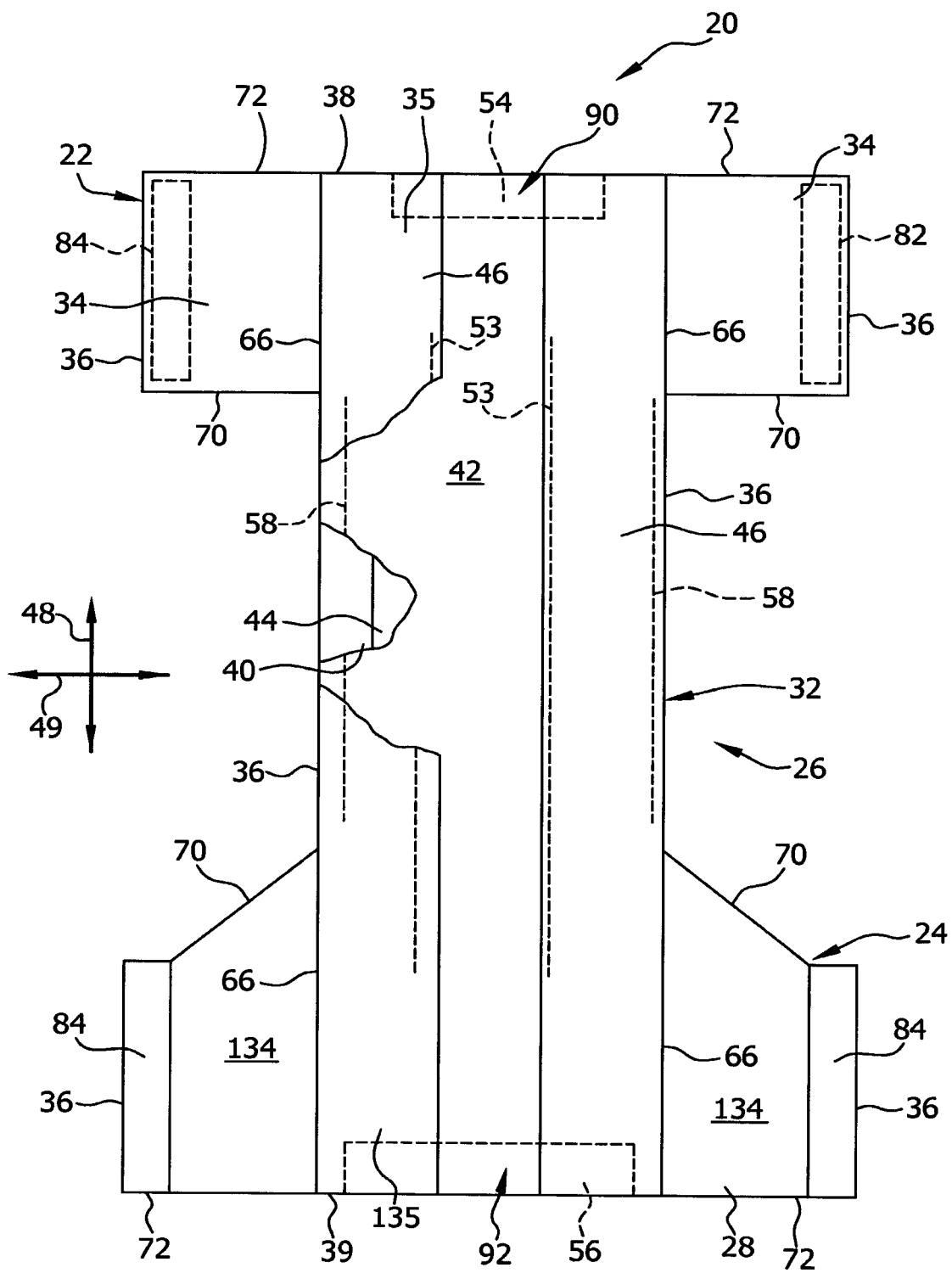
FIG. 3 is a plan view of an absorbent garment in a stretched flat state showing the surface of the garment that faces the wearer when the garment is worn, and with portions cut away to show the underlying features.

"Longitudinal" and "transverse" have their customary meaning, as indicated by the longitudinal and transverse axes depicted in FIGS. 2 and 3. The longitudinal axis lies in the plane of the article and is generally parallel to a vertical plane that bisects a standing wearer into left and right body halves when the article is worn. The transverse axis lies in the plane of the article generally perpendicular to the longitudinal axis. The article as illustrated is generally longer in the longitudinal direction than in the transverse direction, although products longer in the transverse direction are also possible.

"Longitudinal midline" refers to a line, either real or imaginary, that runs along the longitudinal length of the chassis of an absorbent garment and bisects the chassis into two halves of equal transverse width.

"Meltblown fiber" means fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed for example, in U.S. Pat. No. 3,849,241 to Butin et al. Meltblown fibers are microfibers which may be continuous or discontinuous, are generally smaller than about 0.6 denier, and are generally self bonding when deposited onto a collecting surface. Meltblown fibers used in the present invention are preferably substantially continuous in length.

"Member" when used in the singular can have the dual meaning of a single element or a plurality of elements.

"Nonwoven" and "nonwoven web" refer to materials and webs of material which are formed without the aid of a textile weaving or knitting process.

"Offset tucked" refers to a folded position of a garment wherein the front and back regions of the garment are skewed such that the longitudinal midline of the front region of the chassis is offset or not aligned with the longitudinal midline of the back region of the chassis, and seams connecting the front and back regions are tucked.

"Operatively joined," in reference to the attachment of an elastic member to another element, means that the elastic member when attached to or connected to the element, or treated with heat or chemicals, by stretching, or the like, gives the element elastic properties; and with reference to the attachment of a non-elastic member to another element, means that the member and element can be attached in any suitable manner that permits or allows them to perform the intended or described function of the joinder. The joining, attaching, connecting or the like can be either directly, such as joining either member directly to an element, or can be indirectly by means of another member disposed between the first member and the first element.

"Overlapped tucked" refers to a folded position of a garment wherein extraneous portions of the garment, each having at least one seam, are folded such that the extraneous portions overlap one another.

"Permanently attached" or "permanently bonded" refers to the joining, adhering, connecting, attaching, bonding, or the like, of two elements of an absorbent garment such that the elements tend to be and remain attached during normal use conditions of the absorbent garment.

"Polymers" include, but are not limited to, homopolymers, copolymers, such as for example, block, graft, random and alternating copolymers, terpolymers, etc. and blends and modifications thereof. Furthermore, unless otherwise specifically limited, the term "polymer" shall include all possible geometrical configurations of the material. These configurations include, but are not limited to isotactic, syndiotactic and atactic symmetries.

"Refastenable" refers to the property of two elements being capable of releasable attachment, separation, and subsequent releasable reattachment without substantial permanent deformation or rupture. The refastenable elements can be attached, separated and reattached for at least one cycle, suitably for at least 5 cycles, or suitably for at least 10 cycles.

"Releasably attached," "releasably engaged" and variations thereof refer to two elements being connected or connectable such that the elements tend to remain connected absent a separation force applied to one or both of the elements, and the elements being capable of separation without substantial permanent deformation or rupture. The required separation force is typically beyond that encountered while wearing the absorbent garment.

"Self-engaging fastener" refers to a fastening component that can engage with another fastening component having the same structure.

"Spunbonded fiber" refers to small diameter fibers which are formed by extruding molten thermoplastic material as filaments from a plurality of fine capillaries of a spinnerette having a circular or other configuration, with the diameter of the extruded filaments then being rapidly reduced as by, for example, in U.S. Pat. No. 4,340,563 to Appel et al., and U.S. Pat. No. 3,692,618 to Dorschner et al., U.S. Pat. 3,802,817 to Matsuki et al., U.S. Pat. Nos. 3,338,992 and 3,341,394 to Kinney, U.S. Pat. No. 3,502,763 to Hartmann, U.S. Pat. No. 3,502,538 to Petersen, and U.S. Pat. No. 3,542,615 to Dobo et al., each of which is incorporated herein in its entirety by reference. Spunbond fibers are quenched and generally not tacky when they are deposited onto a collecting surface. Spunbond fibers are generally continuous and often have average deniers larger than about 0.3, more particularly, between about 0.6 and 10.

"Stretchable" means that a material can be stretched, without breaking, to at least 150% of its initial (unstretched) length in at least one direction, suitably to at least 250% of its initial length, desirably to at least 300% of its initial length.

"Superabsorbent" or "superabsorbent material" refers to a water-swellable, water-insoluble organic or inorganic material capable, under the most favorable conditions, of absorbing at least about 15 times its weight and, more desirably, at least about 30 times its weight in an aqueous solution containing 0.9 weight percent sodium chloride. The superabsorbent materials can be natural, synthetic and modified natural polymers and materials. In addition, the superabsorbent materials can be inorganic materials, such as silica gels, or organic compounds such as cross-linked polymers.

"Surface" includes any layer, film, woven, nonwoven, laminate, composite, or the like, whether pervious or impervious to air, gas, and/or liquids.

"Thermoplastic" describes a material that softens when exposed to heat and which substantially returns to a non-softened condition when cooled to room temperature.

"Tucked" refers to a folded state of a garment in which at least one portion of the garment is folded to create a more compact orientation of the garment. The folded state can include a fold inserted into the chassis or a fold over or under the chassis.

These terms may be defined with additional language in the remaining portions of the specification.

DETAILED DESCRIPTION OF THE PRESENTLY PREFERRED EMBODIMENTS

The present invention is directed to refastenable seams on garments in a tucked position. A flat orientation of resilient fastening components in the tucked position prevents creases from occurring in the fastening components, thereby preserving the available fastener seam strength and making the fasteners less likely to disengage during product application and wear.

The principles of the present invention can be incorporated into any suitable disposable absorbent article having a pre-fastened and refastenable seam. Examples of such suitable articles include diapers, training pants, incontinence products, other personal care or health care garments, including medical garments, or the like. As used herein, the term "incontinence products" includes absorbent underwear for children, absorbent garments for children or young adults with special needs such as autistic children or others with bladder/bowel control problems as a result of physical disabilities, as well as absorbent garments for incontinent older adults. For ease of explanation, the description hereafter will be in terms of a child's training pant.

Referring to FIG. 1, a disposable absorbent article, such as a training pant 20, is illustrated in a partially fastened condition. The training pant 20 includes two refastenable seams 80, each extending from a waist opening 50 to one of two leg openings 52 on opposing sides of the garment 20. Each seam 80 includes a fastening component 82 and a mating fastening component 84. Either the fastening component 82 or the mating fastening component 84, or both, is a resilient fastening component. The term "resilient" as used herein refers to an interlocking material having a predetermined shape and the property of the interlocking material to resume the predetermined shape after being engaged and disengaged from a mating, complementary interlocking material. The resilient fastener may be deformed under great stress, such as during compression, particularly when the fastener does not lie in a flat plane. Resilient fastening components are typically formed from resilient material and have a backing and a plurality of engaging elements that project from the backing. An example of a suitable resilient fastening component is a hook type fastener that can repeatedly be engaged with and released from a loop type fastener.

It has been found that fastener performance can be compromised when a resilient fastening component in a refastenable seam is creased during processing or compression in preparation for or during packaging. Usually, creases in fastening components formed during packaging and storage do not completely unfold or disappear during subsequent use of the garment. A crease or creases in a fastener hook component can deform individual hooks or the underlying material. The result of either deformation can be reduced engagement ability due either to deadened hooks or to spacing between hooks and loop material that prevent hooks from engaging in the loop material. When any hooks on a hook component are deadened, the engageable area of the hook component is reduced. As a result, a creased fastener tends to possess lower peel and/or shear values than uncreased fasteners. Products with severe and/or multiple fastener creases tend to be most apt to pop open during application and wear due to a greater number of deadened engagement elements. Creases can also hinder performance of fastener loop materials by flattening some of the loops, and by spacing some of the loops farther away from the hook material.

Fastener creases appear to be more of an issue for hook components than for loop components due to the potential permanent deformation of hook material compared to the relative flexibility of loop material. A major cause of these performance-impairing creases in refastenable seams is believed to be attributable to the orientation of the resilient fastening component before and/or during product compression, and before and/or during packaging.

The tucked orientation of the refastenable seams 80 of the present invention in preparation for and/or during packaging prevents fastener creases from occurring, thus preserving the available fastener seam strength and making fasteners, such as hook and loop fasteners, less likely to disengage during product application and wear. A detailed description of the tucked orientation of the refastenable seams 80 during packaging follows a description of the garment 20 below.

Referring again to FIG. 1, the training pant 20 includes an absorbent chassis 32 defining a front region 22, a back region 24, a crotch region 26 interconnecting the front and back regions, an inner surface 28 which is configured to contact the wearer, and an outer surface 30 opposite the inner surface which is configured to contact the wearer's clothing. With additional reference to FIGS. 2 and 3, the absorbent chassis 32 also defines a pair of transversely opposed distal edges 36 and a pair of longitudinally opposed waist edges, which are designated front waist edge 38 and back waist edge 39. The front region 22 is contiguous with the front waist edge 38, and the back region 24 is contiguous with the back waist edge 39. The chassis 32 also includes a pair of transversely opposed front side panels 34 and a pair of transversely opposed back side panels 134. The front and back side panels 34, 134 are formed along the distal edges 36 of the chassis and can either be integrally formed with the chassis, as shown in FIG. 2, or can each include at least one separate element permanently attached to the chassis, as shown in FIGS. 1 and 3. For reference, arrows 48 and 49 depicting the orientation of the longitudinal axis and the transverse axis, respectively, of the training pant 20 are illustrated in FIGS. 2 and 3.

The illustrated absorbent chassis 32 can include an outer cover 40, a bodyside liner 42 which is connected to the outer cover in a superposed relation, an absorbent assembly 44 which is located between the outer cover 40 and the bodyside liner 42, and a pair of containment flaps 46, as shown in FIG. 3.

Figure 4:
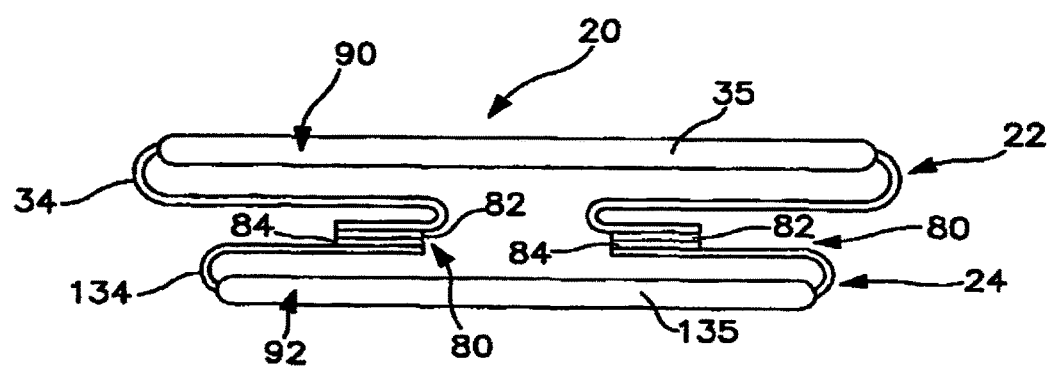
FIG. 4 is a top view of a waist region of an absorbent garment in which the refastenable seams are in a differential tucked position.
Figure 5:
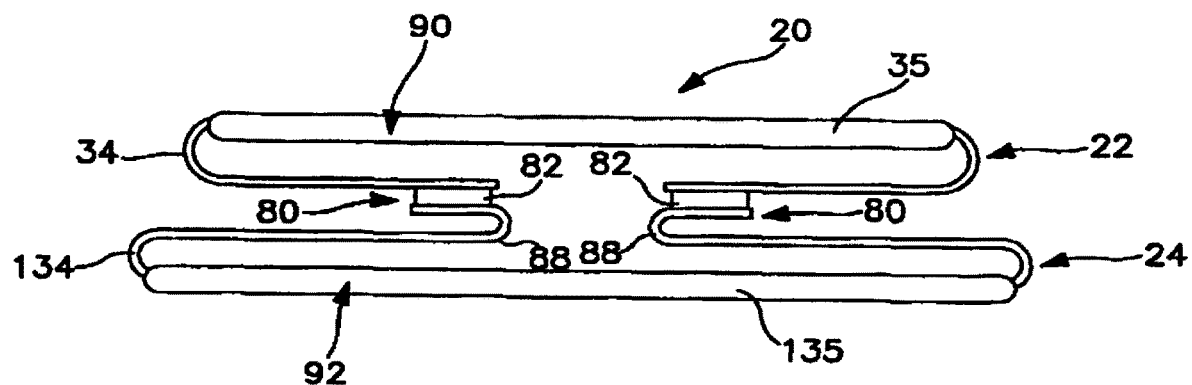
FIG. 5 is a top view of a waist region of an absorbent garment in which the refastenable seams are in a differential tucked position.
Figure 12:
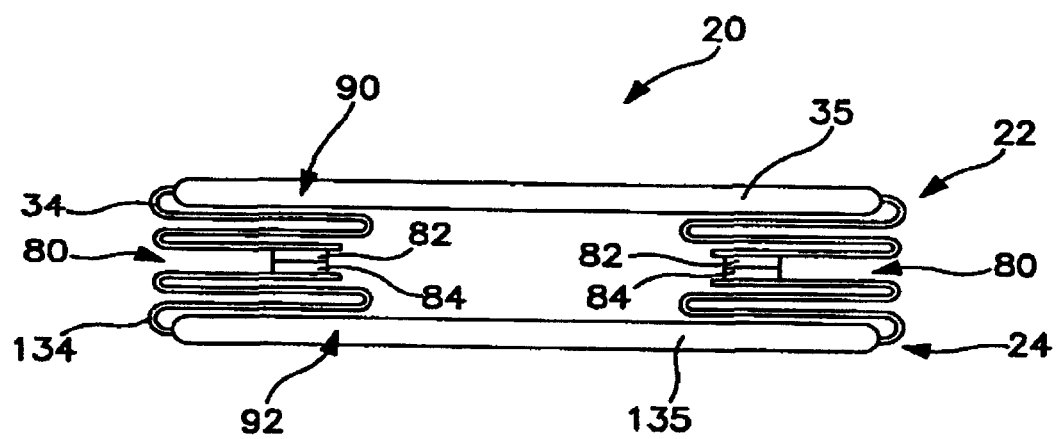
FIG. 12 is a top view of a waist region of an absorbent garment in which the refastenable seams are in a differential tucked position.
Figure 13:
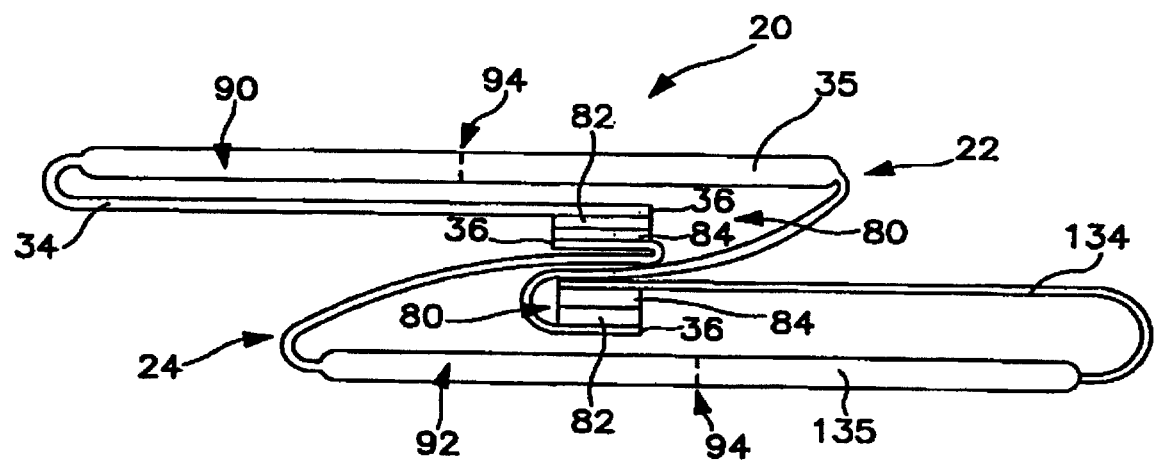
FIG. 13 is a top view of a waist region of an absorbent garment in which the refastenable seams are in an offset tucked position.
Figure 14:
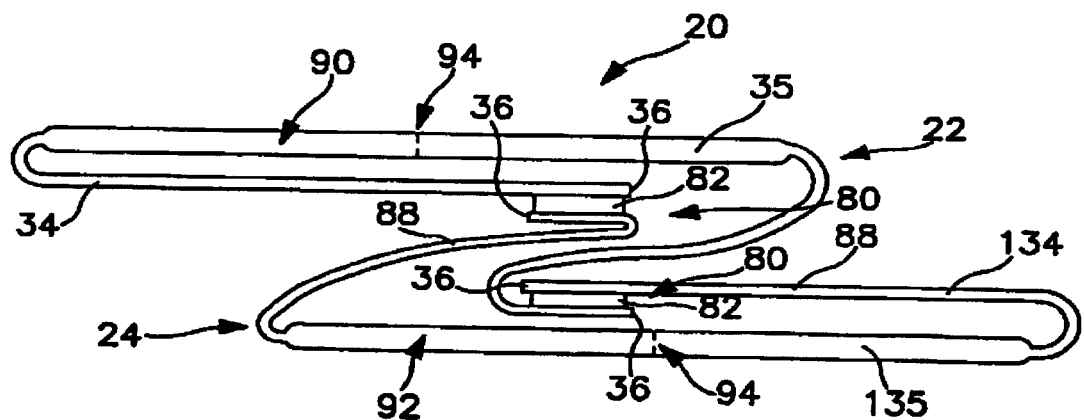
FIG. 14 is a top view of a waist region of an absorbent garment in which the refastenable seams are in an offset tucked position.
Figure 16:
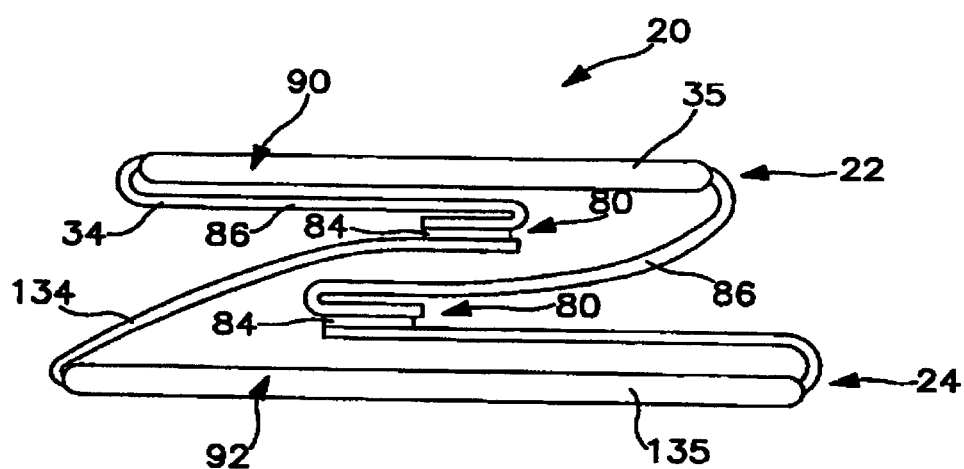
FIG. 16 is a top view of a waist region of an absorbent garment in which the refastenable seams are in an overlapped tucked position.
Figure 17:
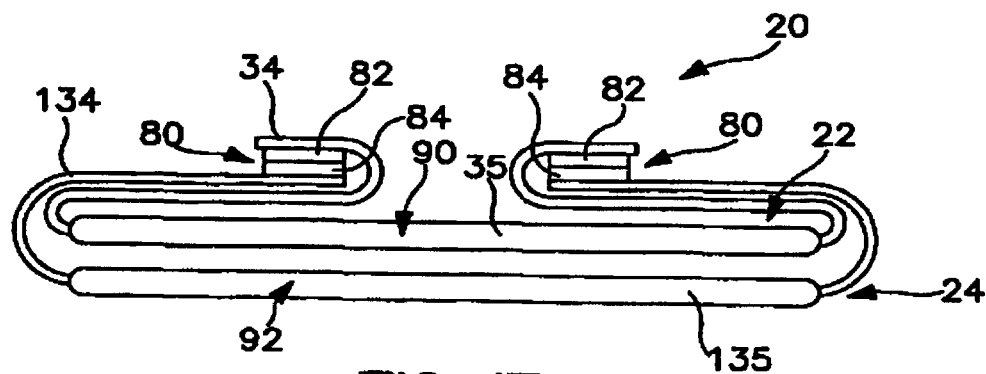
FIG. 17 is a top view of a waist region of an absorbent garment in which the refastenable seams are folded outside of the front panel of the chassis.
Figure 18:
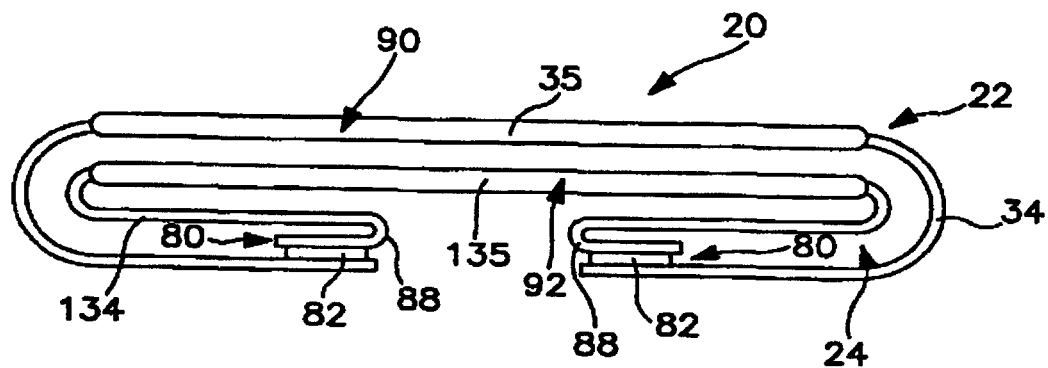
FIG. 18 is a top view of a waist region of an absorbent garment in which the refastenable seams are folded outside of the back panel of the chassis.

The front side panels 34 shown in FIGS. 4-19, each include fastening components incorporated therein, either in the form of separate fastening components 82, as shown in FIGS. 4, 5, 7, 9-15, 17 and 18, or in the form of fastening material 86 forming at least a portion of the side panels 34, as shown in FIGS. 6, 8, 16 and 19, such that one fastening component on each side panel 34 can be releasably engaged with a mating fastening component incorporated into each back side panel 134. Similarly, the mating fastening components can be in the form of either separate mating fastening components 84, as shown in FIGS. 4, 6-13, 15-17 and 19, or in the form of mating fastening material 88 forming at least a portion of the chassis 32, as shown in FIGS. 5, 14 and 18. In various embodiments, either the entire outer cover 40 or the entire body side liner 42 or the front side panels 34 or the back side panels 134 can be made of a fastening material 86 or a mating fastening material 88.

With the training pant 20 in the fastened position, as partially illustrated in FIG. 1, the front and back regions 22 and 24 are joined together to define a three-dimensional pant configuration having a waist opening 50 and a pair of leg openings 52. The front region 22 includes the portion of the training pant 20 which, when worn, is positioned on the front of the wearer while the back region 24 includes the portion of the training pant which, when worn, is positioned on the back of the wearer. The crotch region 26 of the training pant 20 includes the portion of the training pant which, when worn, is positioned between the legs of the wearer and covers the lower torso of the wearer. The front and back side panels 34, 134 include the portions of the training pant 20 which, when worn, are positioned on the hips of the wearer.

As shown in FIG. 3, the front region 22 of the absorbent chassis 32 includes the transversely opposed front side panels 34 and a front panel 35 positioned between and interconnecting the side panels, along with a front waist elastic member 54 and any other connected components. A front waist region 90 is a region of the front panel 35 along the front waist edge 38. The back region 24 of the absorbent chassis 32 includes the transversely opposed back side panels 134 and a back panel 135 positioned between and interconnecting the side panels, as well as a rear waist elastic member 56 and any other connected components. A back waist region 92 is a region of the back panel 135 along the back waist edge 39. The waist edges 38 and 39 of the absorbent chassis 32 are configured to encircle the waist of the wearer when worn and provide the waist opening 50 which defines a waist perimeter dimension. Portions of the transversely opposed distal edges 36 of the chassis 32 in the crotch region 26, along with leg end edges 70 of the side panels 34 and 134, generally define the leg openings 52.

The absorbent chassis 32 is configured to contain and/or absorb any body exudates discharged from the wearer. For example, the absorbent chassis 32 desirably, although not necessarily, includes the pair of containment flaps 46 which are configured to provide a barrier to the transverse flow of body exudates. A flap elastic member 53 (FIG. 3) can be operatively joined with each containment flap 46 in any suitable manner as is well known in the art. The elasticized containment flaps 46 define an unattached edge which assumes an upright, generally perpendicular configuration in at least the crotch region 26 of the training pant 20 to form a seal against the wearer's body. The containment flaps 46 can be located along the transversely opposed distal edges 36 of the absorbent chassis 32, and can extend longitudinally along the entire length of the absorbent chassis or may only extend partially along the length of the absorbent chassis. Suitable constructions and arrangements for the containment flaps 46 are generally well known to those skilled in the art and are described in U.S. Pat. No. 4,704,116 issued Nov. 3, 1987 to Enloe, which is incorporated herein by reference.

To further enhance containment and/or absorption of body exudates, the training pant 20 can include the front waist elastic member 54, the rear waist elastic member 56, and leg elastic members 58, as are known to those skilled in the art (FIG. 3). The waist elastic members 54 and 56 can be operatively joined to the outer cover 40 and/or bodyside liner 42 along the opposite waist edges 38 and 39 as well as over waist edges 72 of the side panels 34, 134, and can extend over part or all of the waist edges. The leg elastic members 58 can be operatively joined to the outer cover 40 and/or bodyside liner 42 while longitudinally aligned along the distal edges 36 and positioned in the crotch region 26 of the chassis 32.

The flap elastic members 53, the waist elastic members 54 and 56, and the leg elastic members 58 can be formed of any suitable elastic material. As is well known to those skilled in the art, suitable elastic materials include sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example with the application of heat; such that elastic constrictive forces are imparted to the substrate. In one particular embodiment, for example, the leg elastic members 58 include a plurality of dry-spun coalesced multifilament spandex elastomeric threads (e.g, LYCRA threads) and available from E.I. DuPont de Nemours and Company, Wilmington, Del., U.S.A.

The outer cover 40 desirably includes a material that is substantially liquid impermeable, and can be elastic, stretchable or nonstretchable. The outer cover 40 can be a single layer of liquid impermeable material, but desirably includes a multi-layered laminate structure in which at least one of the layers is liquid impermeable. For instance, the outer cover 40 can include a liquid permeable outer layer and a liquid impermeable inner layer that are suitably joined together thermally, ultrasonically, by a laminate adhesive, or by any other suitable methods known in the art. Suitable laminate adhesives, which can be applied continuously or intermittently as beads, a spray, parallel swirls, or the like, can be obtained from Findley Adhesives, Inc., of Wauwatosa, Wis., U.S.A., or from National Starch and Chemical Company, Bridgewater, N.J., U.S.A. The liquid permeable outer layer can be any suitable material and desirably one that provides a generally cloth-like texture and/or mating fastening component qualities. One example of such a material is a 20 gsm (grams per square meter) spunbond polypropylene nonwoven web. The outer layer may also be made of those materials of which liquid permeable bodyside liner 42 is made. While it is not a necessity for the outer layer to be liquid permeable, it is desired that it provides a relatively cloth-like texture to the wearer.

The inner layer of the outer cover 40 can be both liquid and vapor impermeable, or can be liquid impermeable and vapor permeable. The inner layer is desirably manufactured from a thin plastic film, although other flexible liquid impermeable materials may also be used. The inner layer, or the liquid impermeable outer cover 40 when a single layer, prevents waste material from wetting articles, such as bedsheets and clothing, as well as the wearer and care giver. A suitable liquid impermeable film for use as a liquid impermeable inner layer, or a single layer liquid impermeable outer cover 40, is a 0.2 millimeter polyethylene film commercially available from Huntsman Packaging of Newport News, Va., U.S.A. If the outer cover 40 is a single layer of material, it can be embossed and/or matte finished to provide a more cloth-like appearance. As earlier mentioned, the liquid impermeable material can permit vapors to escape from the interior of the disposable absorbent article, while still preventing liquids from passing through the outer cover 40. A suitable "breathable" material is composed of a microporous polymer film or a nonwoven fabric that has been coated or otherwise treated to impart a desired level of liquid impermeability. A suitable microporous film is a PMP-1 film material commercially available from Mitsui Toatsu Chemicals, Inc., Tokyo, Japan, or an XKO-8044 polyolefin film commercially available from 3M Company, Minneapolis, Minn.

The liquid permeable bodyside liner 42 is illustrated as overlying the outer cover 40 and absorbent assembly 44, and may but need not have the same dimensions as the outer cover 40. The bodyside liner 42 is desirably compliant, soft feeling, and non-irritating to the child's skin. Further, the bodyside liner 42 can be less hydrophilic than the absorbent assembly 44, to present a relatively dry surface to the wearer and permit liquid to readily penetrate through its thickness. As mentioned, the bodyside liner 42 and/or the outer cover 40 can be made of a fastening component material or a mating fastening component material to eliminate the need for separately attached mating fastening components.

The bodyside liner 42 can be manufactured from a wide selection of web materials, such as synthetic fibers (for example, polyester or polypropylene fibers), natural fibers (for example, wood or cotton fibers), a combination of natural and synthetic fibers, porous foams, reticulated foams, apertured plastic films, or the like. Various woven and nonwoven fabrics can be used for the bodyside liner 42. For example, the bodyside liner can be composed of a meltblown or spunbonded web of polyolefin fibers. The bodyside liner can also be a bonded-carded web composed of natural and/or synthetic fibers. The bodyside liner can be composed of a substantially hydrophobic material, and the hydrophobic material can, optionally, be treated with a surfactant or otherwise processed to impart a desired level of wettability and hydrophilicity. For example, the material can be surface treated with about 0.45 weight percent of a surfactant mixture including AHCOVEL N-62 base from Uniqema, Inc., a division of ICI of New Castle, Del., and GLUCOPON 220UP surfactant from Cognis Corp. of Ambler, Pa., in an active ratio of 3:1. The surfactant mixture can be applied by any conventional means, such as spraying, printing, brush coating or the like. The surfactant mixture can be applied to the entire bodyside liner 42 or can be selectively applied to particular sections of the bodyside liner, such as the medial section along the longitudinal centerline.

A suitable liquid permeable bodyside liner 42 is a nonwoven bicomponent web having a basis weight of about 27 gsm. The nonwoven bicomponent can be a spunbond bicomponent web, or a bonded carded bicomponent web. Suitable bicomponent staple fibers include a polyethylene/polypropylene bicomponent fiber available from Chisso Corporation, Osaka, Japan. In this particular bicomponent fiber, the polypropylene forms the core and the polyethylene forms the sheath of the fiber. Other fiber orientations are possible, such as multi-lobe, side-by-side, end-to-end, or the like. While the outer cover 40 and bodyside liner 42 can include elastomeric materials, it can be desirable in some embodiments for the composite structure to be generally inelastic, where the outer cover, the bodyside liner and the absorbent assembly include materials that are generally not elastomeric.

The absorbent assembly 44 (FIG. 3) is positioned between the outer cover 40 and the bodyside liner 42, which components can be joined together by any suitable means, such as adhesives, as is well known in the art. The absorbent assembly 44 can be any structure which is generally compressible, conformable, non-irritating to the child's skin, and capable of absorbing and retaining liquids and certain body wastes. The absorbent assembly 44 can be manufactured in a wide variety of sizes and shapes, and from a wide variety of liquid absorbent materials commonly used in the art. For example, the absorbent assembly 44 can suitably include a matrix of hydrophilic fibers, such as a web of cellulosic fluff, mixed with particles of a high-absorbency material commonly known as superabsorbent material. High absorbency material can be provided in any form known in the art, including but not limited to particles, fibers, foams and films.

In a particular embodiment, the absorbent assembly 44 includes a matrix of cellulosic fluff, such as wood pulp fluff, and superabsorbent hydrogel-forming particles. The wood pulp fluff can be exchanged with synthetic, polymeric, meltblown fibers or with a combination of meltblown fibers and natural fibers. The superabsorbent particles can be substantially homogeneously mixed with the hydrophilic fibers or can be nonuniformly mixed. The fluff and superabsorbent particles can also be selectively placed into desired zones of the absorbent assembly 44 to better contain and absorb body exudates. The concentration of the superabsorbent particles can also vary through the thickness of the absorbent assembly 44. Alternatively, the absorbent assembly 44 can include a laminate of fibrous webs and superabsorbent material or other suitable means of maintaining a superabsorbent material in a localized area.

Suitable superabsorbent materials can be selected from natural, synthetic, and modified natural polymers and materials. The superabsorbent materials can be inorganic materials, such as silica gels, or organic compounds, such as crosslinked polymers. Suitable superabsorbent materials are available from various commercial vendors, such as Dow Chemical Company located in Midland, Mich., U.S.A., and Stockhausen GmbH & Co. KG, D-47805 Krefeld, Federal Republic of Germany. Typically, a superabsorbent material is capable of absorbing at least about 15 times its weight in water, and desirably is capable of absorbing more than about 25 times its weight in water.

In one embodiment, the absorbent assembly 44 is generally rectangular in shape, and includes a blend of wood pulp fluff and superabsorbent material. One preferred type of fluff is identified with the trade designation CR1654, available from U.S. Alliance, Childersburg, Ala., U.S.A., and is a bleached, highly absorbent sulfate wood pulp containing primarily soft wood fibers. As a general rule, the superabsorbent material is present in the absorbent assembly 44 in an amount of from about 0 to about 90 weight percent based on total weight of the absorbent assembly. The absorbent assembly 44 suitably has a density within the range of about 0.10 to about 0.50 grams per cubic centimeter. The absorbent assembly 44 may or may not be wrapped or encompassed by a suitable tissue wrap that maintains the integrity and/or shape of the absorbent assembly.

The absorbent chassis 32 can also incorporate other materials that are designed primarily to receive, temporarily store, and/or transport liquid along the mutually facing surface with the absorbent assembly 44, thereby maximizing the absorbent capacity of the absorbent assembly. One suitable material is referred to as a surge layer (not shown) and includes a material having a basis weight of about 50 to about 120 grams per square meter, and including a through-air-bonded-carded web of a homogenous blend of 60 percent 3 denier type T-256 bicomponent fiber including a polyester core/polyethylene sheath and 40 percent 6 denier type T-295 polyester fiber, both commercially available from Kosa Corporation of Salisbury, N.C., U.S.A.

As noted previously, the illustrated training pant 20 has front and back side panels 34, 134 disposed on each side of the absorbent chassis 32. These transversely opposed front side panels 34 and transversely opposed back side panels 134 can be permanently bonded to the front panel 35 and back panel 135 in the respective front and back regions 22, 24 along attachment lines 66, and are releasably attached to one another. The side panels 34, 134 may be permanently attached using attachment means known to those skilled in the art such as adhesive, thermal or ultrasonic bonding. As mentioned, the side panels 34, 134 can also be formed as continuous extensions of the front and back panels 35, 135.

As shown in FIGS. 1 and 4-19, the fastening components 82 can be permanently bonded to either the inner surface 28 or the outer surface 30 of each front side panel 34 adjacent each distal edge 36 of the front region 22 of the chassis 32, and the mating fastening components 84 can be permanently bonded to either the inner surface 28 or the outer surface 30 of each back side panel 134 adjacent each distal edge 36 of the back region 24 of the chassis, or either the inner surface 28 or the outer surface 30 of the chassis 32 can include fastening material 86 or mating fastening material 88. The fastening components 82 and the mating fastening components 84 may be attached to the side panels 34 and the chassis 32 using attachment means known to those skilled in the art such as adhesive, thermal or ultrasonic bonding.

In one particular embodiment, the fastening components 82 each include hook type fasteners and the mating fastening components 84 each include complementary loop type fasteners. In another particular embodiment, the fastening components 82 each include loop type fasteners and the mating fastening components 84 each include complementary hook type fasteners. In yet another embodiment, half of the fastening components 82 and half of the mating fastening components 84 can include hook type fasteners, while half of the fastening components 82 and half of the mating fastening components 84 can include loop type fasteners. In still another embodiment, each of the fastening components 82 and the mating fastening components 84 include self-engaging fasteners. The fastening components 82 and the mating fastening components 84 are desirably rectangular, although they may alternatively be square, round, oval, curved, discontinuous such as multiple fasteners, or any other suitable shape. The fastening components 82 and mating fastening components 84 may or may not be parallel to a longitudinal midline 94 of the garment 20.

In another embodiment, the nonwoven web in the outer cover 40 can be constructed of a material that is suitable for use as a loop-type fastening material, thereby eliminating the need for separate loop-type fastening components 82 or 84, and the fastening components 82 or 84 on the side panels 34 or 134 can be hook-type fastening components. In yet another embodiment, the nonwoven web in the bodyside liner 42 can be constructed of a material that is suitable for use as a loop-type fastening material, thereby eliminating the need for separate loop-type fastening components 82 or 84, and the fastening components 82 or 84 on the side panels 34 or 134 can be hook-type fastening components. In still another embodiment, an inner or outer surface of either the front side panels 34 or the back side panels 134 can include a loop-type fastening material, thereby eliminating the need for separate loop type fastening components 82 or 84.

Loop type fasteners typically include a fabric or material having a base or backing structure and a plurality of loop members extending upwardly from at least one surface of the backing structure. The loop material can be formed of any suitable material, such as acrylic, nylon or polyester, and can be formed by methods such as warp knitting, stitch bonding or needle punching. Suitable loop materials are available from Guilford Mills, Inc., Greensboro, N.C., U.S.A. under the trade designation No. 36549.

Hook type fasteners typically include a fabric or material having a base or backing structure and a plurality of hook members extending upwardly from at least one surface of the backing structure. In contrast to the loop type fasteners which desirably include a flexible fabric, the hook material advantageously includes a resilient material to minimize unintentional disengagement of the fastener components as a result of the hook material becoming deformed and catching on clothing or other items. Suitable hook material can be molded or extruded of nylon, polypropylene or another suitable material. Suitable single-sided hook materials for the fastening components 82 or the mating fastening components 84 are available from commercial vendors such as Velcro Industries B.V., Amsterdam, Netherlands or affiliates thereof, and are identified as Velcro HTH-829 with a uni-directional hook pattern and having a thickness of about 0.9 millimeters (35 mils) and HTH-851 with a uni-directional hook pattern and having a thickness of about 0.5 millimeters (20 mils); and Minnesota Mining & Manufacturing Co., St. Paul, Minn. U.S.A., including specific materials identified as CS-600.

In particular embodiments for improved fit and appearance, the side panels 34, 134 desirably have an average length dimension measured parallel to the longitudinal axis 48 that is about 20 percent or greater, and particularly about 25 percent or greater, of the overall length dimension of the absorbent article, also measured parallel to the longitudinal axis 48. For example, in training pants having an overall length dimension of about 54 centimeters, the side panels 34, 134 desirably have an average length dimension of about 10 centimeters or greater, such as about 15 centimeters. A waist end edge 72 of each side panel 34, 134 can suitably be relatively straight across in the transverse direction while the leg end edge 70 of each side panel 34, 134 can suitably have a curvature, as shown in FIGS. 2 and 3, to allow the leg opening 52 to conform about a wearer's leg.

Each of the side panels 34, 134 can include one or more individual, distinct pieces of material in addition to the fastening components 82, 84, as shown in FIG. 3. In particular embodiments, for example, each side panel 34, 134 can include first and second side panel portions that are joined at a seam, with at least one of the portions including an elastomeric material. The side panels 34, 134 desirably include an elastic material capable of stretching in a direction generally parallel to the transverse axis 49 of the training pant 20. The front side panels 34 and the back side panels 134 can be of equal widths or of different widths in the transverse direction.

Suitable elastic materials, as well as one described process of incorporating elastic side panels into a training pant, are described in the following U.S. Patents: U.S. Pat. No. 4,940,464 issued Jul. 10, 1990 to Van Gompel et al.; U.S. Pat. No. 5,224,405 issued Jul. 6, 1993 to Pohjola; U.S. Pat. No. 5,104,116 issued Apr. 14, 1992 to Pohjola; and U.S. Pat. No. 5,046,272 issued Sep. 10, 1991 to Vogt et al.; all of which are incorporated herein by reference. In particular embodiments, the elastic material includes a stretch-thermal laminate (STL), a neck-bonded laminated (NBL), a reversibly necked laminate, or a stretch-bonded laminate (SBL) material. Methods of making such materials are well known to those skilled in the art and described in U.S. Pat. No. 4,663,220 issued May 5, 1987 to Wisneski et al.; U.S. Pat. No. 5,226,992 issued Jul. 13, 1993 to Morman; and European Patent Application No. EP 0 217 032 published on Apr. 8, 1987 in the names of Taylor et al.; all of which are incorporated herein by reference. Alternatively, the side panel material may include other woven or nonwoven materials, such as those described above as being suitable for the outer cover 40 or bodyside liner 42, or stretchable but inelastic materials.

The desired orientation of the refastenable seams 80 before and/or during compression and/or packaging requires, first, that the seams be pre-fastened, i.e., the fastening component 82 is releasably attached to the mating fastening component 84, and second, that the resilient fastening components, whether attached to the front side panels 34 or the back side panels 134, be situated in a plane parallel to a plane in which the front waist region 90 of the front panel 35 lies. Furthermore, the front waist region 90 and the back waist region 92 lie in parallel planes, thus the plane in which the resilient fastening components lie is also parallel to the plane in which the back waist region 92 lies. In order to achieve this orientation, the side panels 34, 134 must be folded and tucked into or around the chassis 32.

FIG. 4 shows a differential tucked position of the training pant 20, which prevents folding and creasing of the fasteners during packaging of the garment. More specifically, the front side panels 34 are each folded at the edge of the front panel 35, the back side panels 134 are each folded at the edge of the back panel 135, and the fastening components 82 and mating fastening components 84 are aligned such that each fastening component lies in a plane parallel to the front waist region 90 and also parallel to the back waist region 92. In order to achieve this configuration, the front side panels 34 are folded at least twice, both at the edge of the front panel 35 and at or near the edge of the fastening component 82. Alternatively, instead of the front side panels 34 being folded twice, the back side panels 134 can be folded twice, as shown in FIG. 5. The resilient fastening components, whether they are the fastening components 82 or the mating fastening components 84, can be releasably attached directly to the corresponding side panel if the side panel (e.g. 134) is made of an engageable material 88, e.g. loop material, as shown in FIG. 5.

Figure 6:
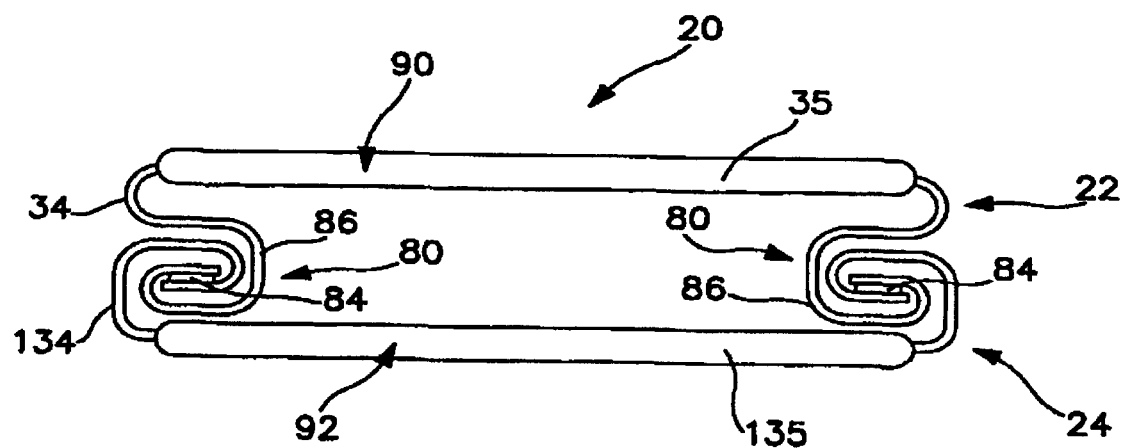
FIG. 6 is a top view of a waist region of an absorbent garment in which the refastenable seams are in a differential tucked position.

FIG. 6 shows another differential tucked position of the training pant 20, in which the front side panels 34 are each folded three times and the back side panels 134 are each folded twice.

Figure 7:
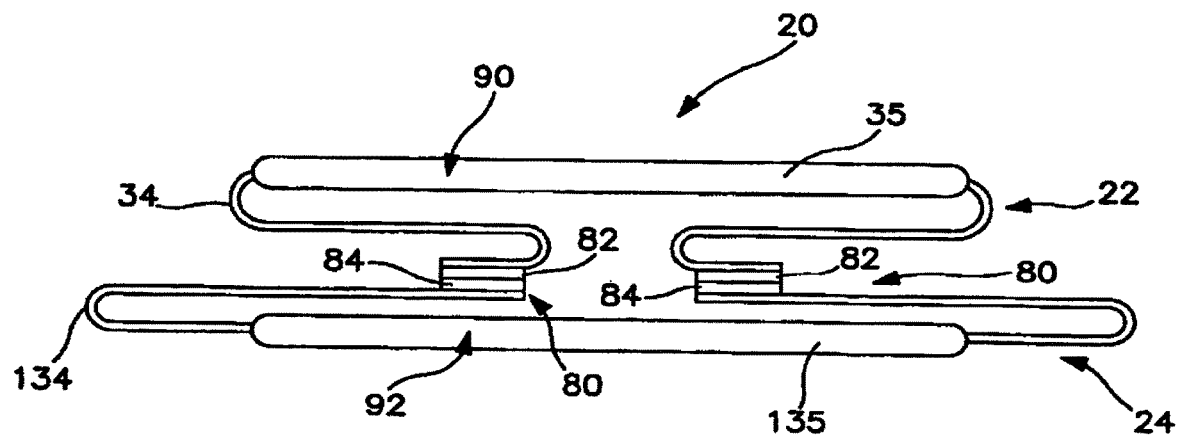
FIG. 7 is a top view of a waist region of an absorbent garment in which the refastenable seams are in a differential undertucked position.
Figure 8:
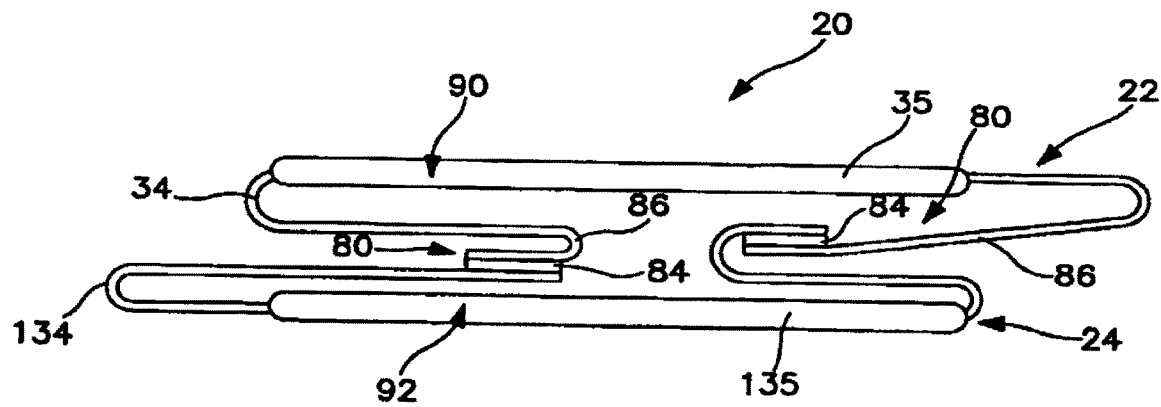
FIG. 8 is top view of a waist region of an absorbent garment in which the refastenable seams are in a differential undertucked position.

FIG. 7 shows a differential undertucked position of the training pant 20. Similar to the differential tucked positions shown in FIGS. 4 and 5, the differential undertucked position includes the front side panels 34 and back side panels 134 each folded, but not necessarily at the edges of the front panel 35 and the back panel 135. Instead, portions of the front side panels 34 and/or the back side panels 134 project beyond the edges of the front panel and/or the back panel, such that the front side panels and/or the back side panels are not fully tucked between the front and back panels 35, 135 of the chassis 32. This configuration is particularly suitable for garments wherein the front panel 35 is either narrower or wider in the transverse direction than the back panel 135, and/or when the front side panels 34 are either narrower or wider in the transverse direction than the back side panels 134. Nevertheless, the fastening components 82 and the mating fastening components 84 are aligned such that each fastening component lies in a plane parallel to the front waist region 90 and also parallel to the back waist region 92. As in the differential tucked positions, in order to achieve the differential undertucked configuration, the front side panels 34 are folded twice, both at the edge of the front panel 35 or away from the edge of the front panel 35 and at or near the edge of the fastening component 82. Alternatively, instead of the front side panels 34 being folded twice, the back side panels 134 can be folded twice. FIG. 8 shows a differential undertucked position of the training pant 20 wherein the resilient fastening components 84 are releasably attached directly to corresponding side panels made of an engageable material 86, rather than to separately attached loop components. FIG. 8 differs from FIG. 7 also in that one of the front side panels 34 is folded once while the other front side panel 34 is folded twice, and one of the back side panels 134 is folded once while the other back side panel 134 is folded twice.

Figure 9:
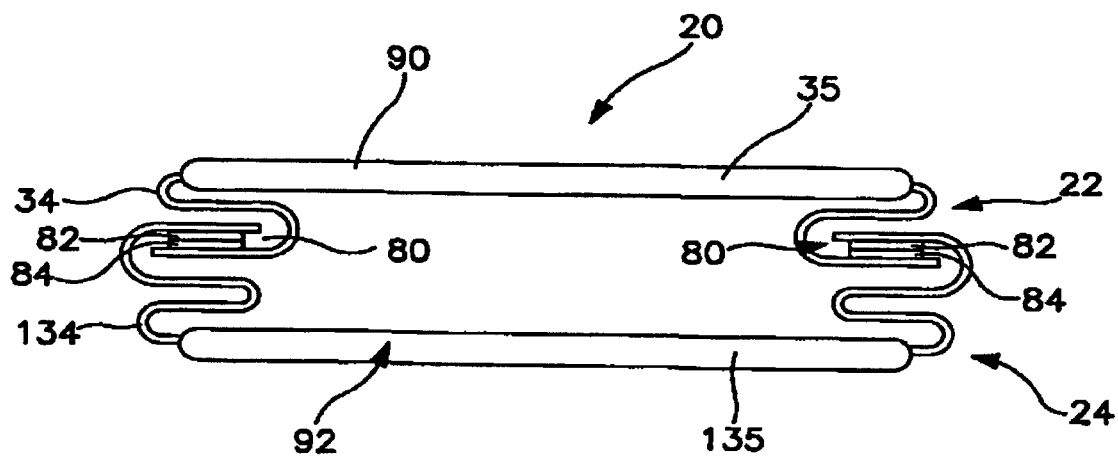
FIG. 9 is a top view of a waist region of an absorbent garment in which the refastenable seams are in a differential tucked position.
Figure 10:
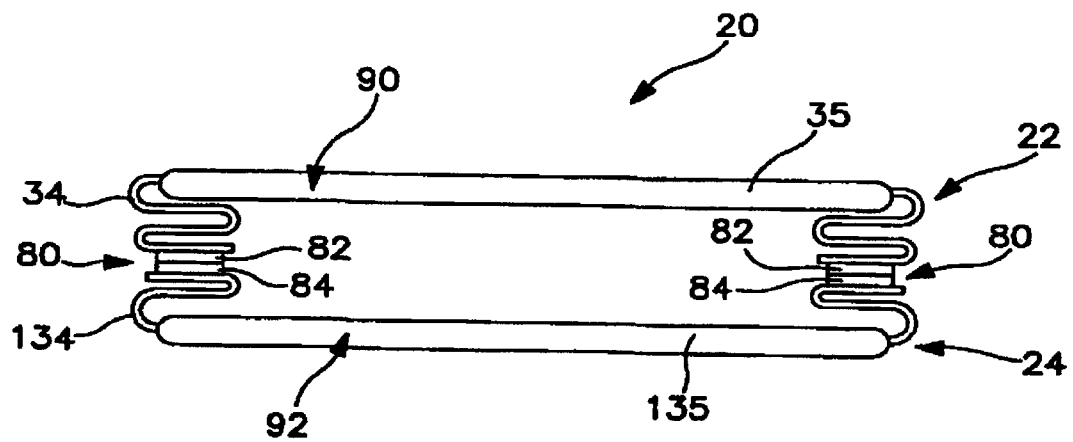
FIG. 10 is a top view of a waist region of an absorbent garment in which the refastenable seams are in a differential tucked position.

FIGS. 9 and 10 show differential tucked positions of the training pant 20 wherein portions of the side panels 34, 134 may or may not project beyond the edges of the front panel 35 and/or the back panel 135. The front side panels 34, 134 are each folded at the edges of the front panel 35 and the back panel 135. The fastening components 82 and the mating fastening components 84 are aligned such that each fastening component lies in a plane parallel to the front waist region 90 and also parallel to the back waist region 92. The front side panels 34 can be folded twice and the back side panels 134 can be folded three times, as shown in FIG. 9, in order to achieve this configuration. Alternatively, the front side panels 34 can be folded three times and the back side panels 134 can be folded twice, as shown in FIG. 10, in order to achieve this configuration.

Figure 11:
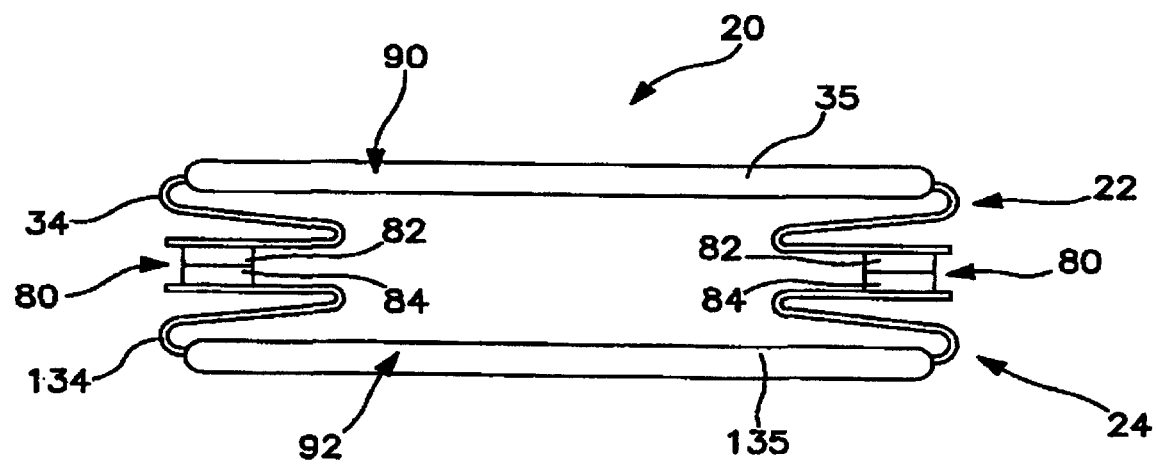
FIG. 11 is a top view of a waist region of an absorbent garment in which the refastenable seams are in a differential tucked position.

FIGS. 11 and 12 show differential tucked positions of the training pant 20 wherein the refastenable seams 80 are butt seams. As used herein, the term "butt seam" refers to a seam wherein two separate pieces of substrate are joined together face-to-face or back-to-back in close proximity to an outer edge of each of the pieces of substrate, and the outer edges of the pieces of substrate project inward or outward from the finished product, as opposed to lying flat, thus placing the seam 80 in peel, as opposed to shearing strain. The fastening components 82 and the mating fastening components 84 are aligned such that each fastening component lies in a plane parallel to the front waist region 90 and also parallel to the back waist region 92. The front side panels 34 and the back side panels 134 can each be folded twice, as shown in FIG. 11, thus creating outward facing refastenable butt seams 80. Alternatively, the front side panels 34 and the back side panels 134 can each be folded three times, as shown in FIG. 12, thus creating inward facing refastenable butt seams 80.

FIG. 13 shows an offset tucked position of the training pant 20. More specifically, the front side panels 34 are each folded at the edge of the front panel 35, the back side panels 134 are each folded at the edge of the back panel 135, and the longitudinal midline 94 of the front panel 35 is offset from the longitudinal midline 94 of the back panel 135. Each fastening component 82 lies in a plane parallel to the front waist region 90 and also parallel to the back waist region 92. In order to achieve this configuration, one front side panel 34 and one back side panel 134 are each folded twice, both at or near the edge of the front panel 35 and back panel 135 and at or near the edge of the fastening component 82 or 84, and one front side panel 34 and one back side panel 134 are each folded once at or near the edge of the front panel 35 and back panel 135. The side panels 34, 134 shown in FIG. 13 are integral with the front and back panels 35, 135, with the fastening components 82, 84 aligned along the distal edges 36 of the front and back regions 22, 24. As in the previous embodiments, the resilient fastening components, whether they are the fastening components 82 or the mating fastening components 84, can be releasably attached directly to the corresponding side panel 34, 134 if the side panel is made of an engageable material 88, e.g. loop material, as shown in FIG. 14.

Figure 15:
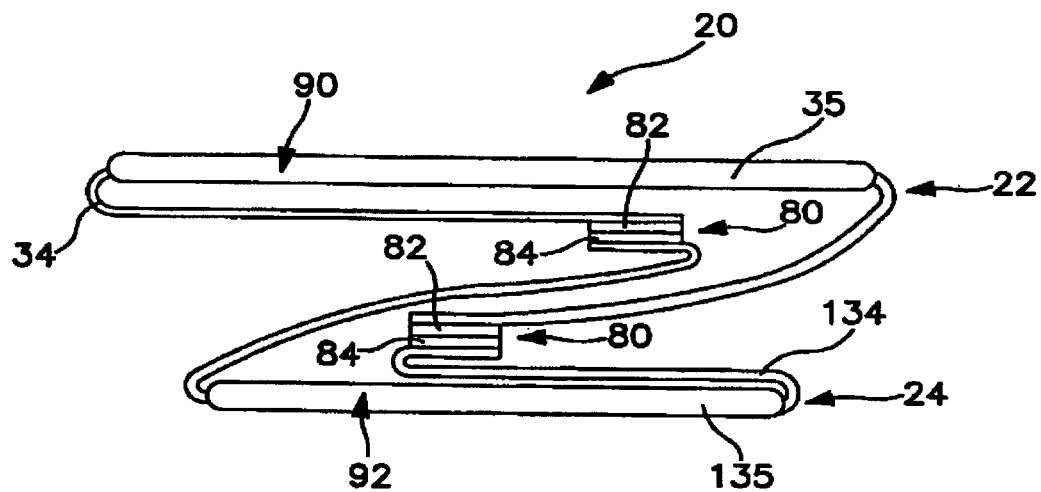
FIG. 15 is a top view of a waist region of an absorbent garment in which the refastenable seams are in an overlapped tucked position.

FIG. 15 shows an overlapped tucked position of the training pant 20. More specifically, the front side panels 34 are each folded at or near the edge of the front panel 35, the back side panels 134 are each folded at or near the edge of the back panel 135, and the fastening components 82 and mating fastening components 84 are aligned such that each fastening component 82, 84 lies in a plane parallel to the front waist region 90 of the front panel 35 and also parallel to the back waist region 92 of the back panel 135. In this position, the refastenable seams 80 are overlapped, such that a seam 80 on a right side of the garment is folded to the left of a seam 80 that is positioned on the left side of the garment. In order to achieve this configuration, the front side panels 34 are folded once at or near the edge of the front panel 35, and the back side panels 134 are folded twice, both at or near the edge of the back panel 135 and at or near the edge of the mating fastening component 84. Alternatively, instead of the front side panels 34 being folded once and the back side panels 134 folded twice, the back side panels 134 can be folded once and the front side panels 34 can be folded twice. The resilient fastening components, whether they are the fastening components 82 or the mating fastening components 84, can be releasably attached directly to the corresponding side panel 34, 134 if the side panel is made of an engageable material 86, e.g. loop material, as shown in FIG. 16.

FIG. 17 shows a tucked position of the training pant 20 wherein the side panels 34, 134 are not positioned between the front panel 35 and the back panel 135. Instead, the refastenable seams 80 are folded onto the front panel 35. More specifically, the front side panels 34 are each folded away from the back panel 135, the back side panels 134 are each folded at or near the edge of the back panel 135 toward the front panel 35, and the fastening components 82 and mating fastening components 84 are aligned such that each fastening component 82, 84 lies in a plane parallel to the front waist region 90 and also parallel to the back waist region 92. In order to achieve this configuration, the front side panels 34 are folded twice, both at or near the edge of the front panel 35 and at or near the edge of the fastening component 82. Alternatively, instead of the refastenable seams 80 being folded onto the front panel 35, the refastenable seams 80 can be folded onto the back panel 135, as shown in FIG. 18. The resilient fastening components, whether they are the fastening components 82 or the mating fastening components 84, can be releasably attached directly to the corresponding side panel 34, 134 if the side panel is made of an engageable material 88, e.g. loop material, as shown in FIG. 18.

Figure 19:
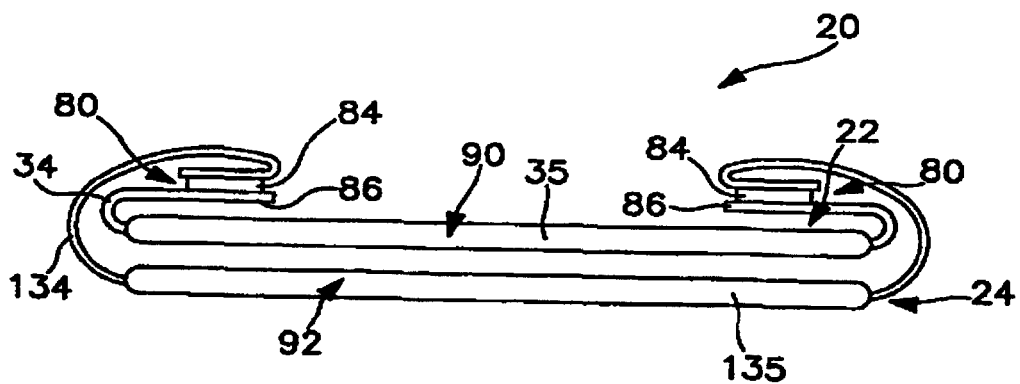
FIG. 19 is a top view of a waist region of an absorbent garment in which the refastenable seams are folded outside of the front panel of the chassis.

FIG. 19 shows a tucked position of the training pant 19 wherein the side panels 34, 134 are folded onto the front panel 35. In this configuration, the front side panels 34 are folded once, at or near the edge of the front panel 35, and the back side panels 134 are folded twice, both at or near the edge of the back panel 135 and at or near the edge of the mating fastening component 84. As shown, the mating fastening components 84 can be releasably attached directly to the front side panels 34 made of an engageable material 86.

Figure 20:
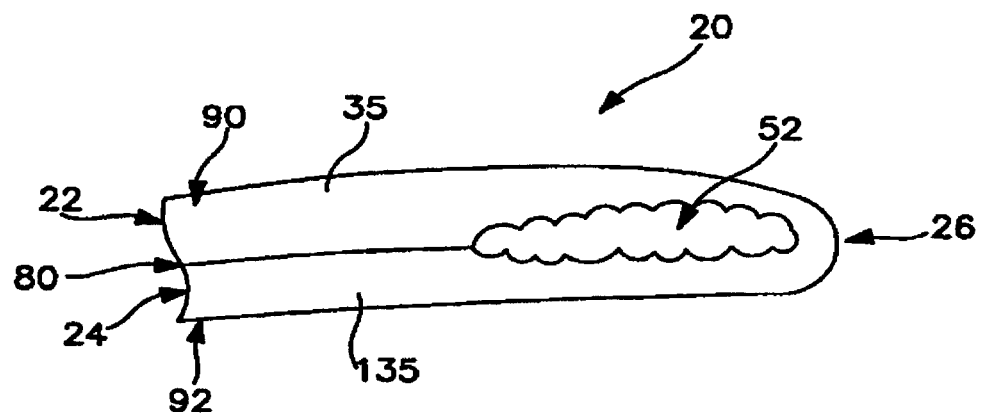
FIG. 20 is a side view of any of the absorbent garments in FIGS. 4-16.
Figure 21:
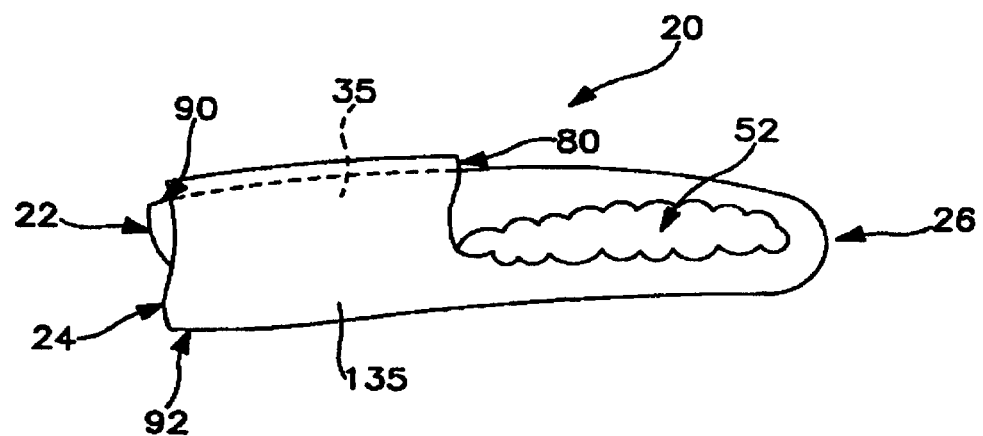
FIG. 21 is a side view of either of the absorbent garments in FIGS. 17 and 19.
Figure 22:
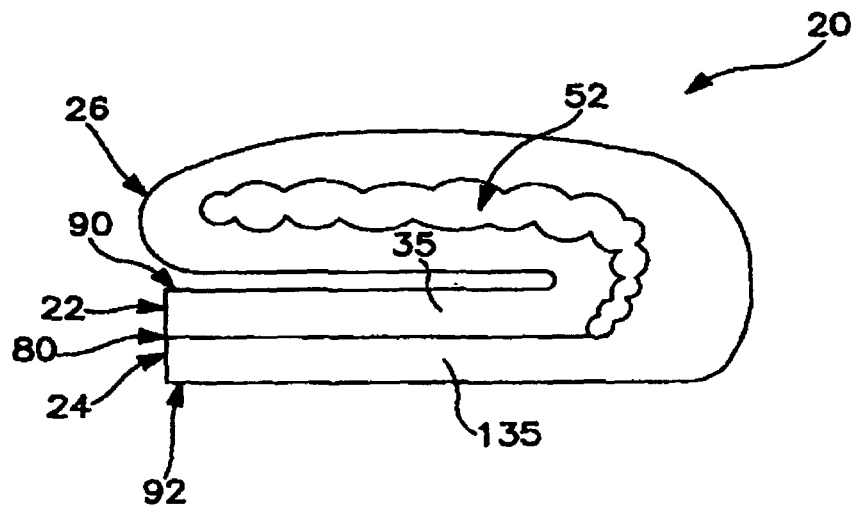
FIG. 22 is a side view of the absorbent garment in FIG. 20 folded once more.
Figure 23:
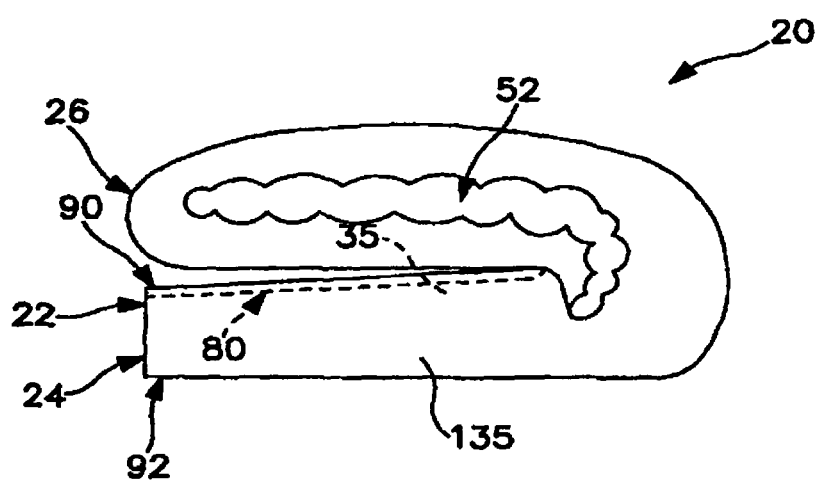
FIG. 23 is a side view of the absorbent garment in FIG. 21 folded once more.
Figure 24:
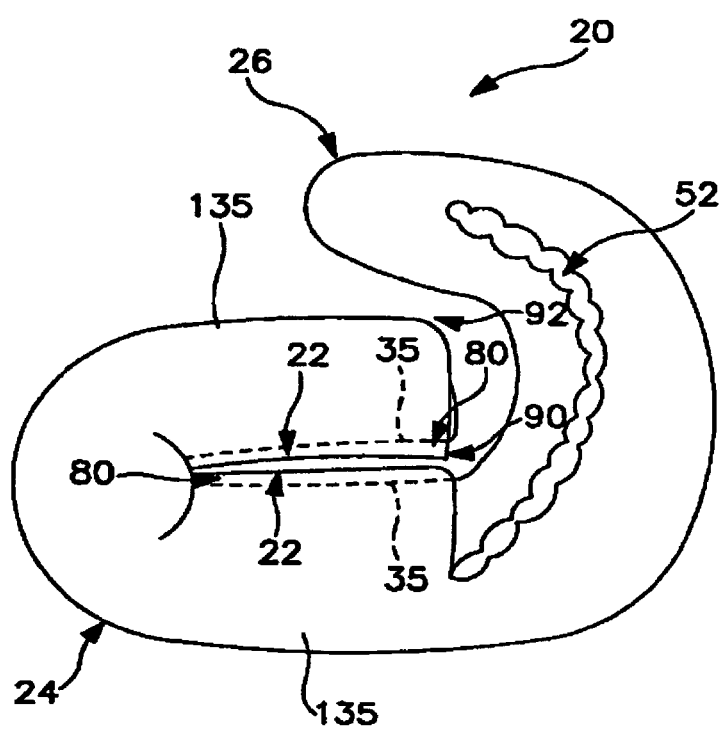
FIG. 24 is a side view of an absorbent garment folded twice in the longitudinal direction.

Each of the orientations of the refastenable seams 80 described above results in a garment 20 having resilient fastening components lying in a plane such that the fastening components will not become creased during packaging. A side view representing any of the garments 20 in FIGS. 4-16 is shown in FIG. 20. A side view representing the garment 20 in FIGS. 17 and 19 is shown in FIG. 21. Any of the configurations shown in FIGS. 4-19 can be folded once again, such that the crotch region 26 of the garment is folded onto either the front region 22 or the back region 24 of the garment, as shown in FIGS. 22 and 23. When folding the garment in this manner, the fold should occur below the refastenable seam 80, such that the refastenable seam remains in a plane parallel to the front and back waist regions 90, 92, as shown in FIGS. 22 and 23. A garment having more than one fastening component 82 and/or 84 along each refastenable seam 80 can be folded between the fastening components 82 and/or 84, and may also be folded below the bottommost fastening components 82, 84, as shown in FIG. 24.

The orientations of the refastenable seams 80 of the present invention are suitable for use with garments of a wide range of sizes and proportions. For example, the orientations can be used with garments 20 having front and back panels 35, 135 of roughly equal transverse widths, or with one of the panels transversely wider than the other. Similarly, the orientations can be used with garments having front and back side panels 34, 134 of roughly equal transverse widths, or with one of the pairs of panels transversely wider than the other. Thus, the refastenable seams 80 of the invention can be located at the exact sides of the garments or can be skewed forward or backward from the exact sides. More particularly, if the front region 22 has a transverse width about equal to a transverse width of the back region 24, the refastenable seams 80 will be located at the exact sides of the garment 20; and if the front region 22 has a transverse width smaller than the transverse width of the back region 24, the refastenable seams 80 will be skewed forward on the garment 20; and if the front region 22 has a transverse width greater than the transverse width of the back region 24, the refastenable seams 80 will be skewed backward on the garment 20. The extent to which the refastenable seams 80 are tucked can be adjusted in order to get the resilient fastening components to lie flat.

As mentioned, the refastenable seams 80 suitably extend longitudinally from the waist opening 50 to the leg openings 52. The refastenable seams 80 can be any suitable transverse width and can vary greatly depending on the product. For example, each refastenable seam 80 can be in a range of about 0.25 inch to about 2.5 inches wide in the transverse direction. As another example, each refastenable seam 80 can be in a range of about 0.5 inch to about 2.0 inches wide in the transverse direction.

Any suitable method can be used to tuck the refastenable seams 80 into the chassis 32. For example, suitable conventional methods include using rotating blades, folding boards and air blasts.

Once the garment 20 is pre-fastened and tucked such that the refastenable seams 80 are oriented in accordance with the present invention, the garment can be compressed and packaged along with multiple other garments of the same kind. Due to the flat orientation of the refastenable seams 80 lying parallel to the flat waist regions 90, 92 of the garment, the resilient fastening components remain flat and do not become creased or crushed when the garment is compressed and packaged. Fastener seam strength is thereby preserved such that the fastening components 82, 84 are less likely to disengage during product application and wear, compared to fastening components that become creased during packaging and compression. A description of compression packing is included in PCT WO 97/49618, published Dec. 31, 1997, the contents of which are hereby incorporated by reference.

It will be appreciated that details of the foregoing embodiments, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

What is claimed is:

1. A pre-fastened, packaged disposable training pant having a longitudinal axis and a transverse axis, the training pant having an unfolded and unfastened configuration prior to packaging and a pre-fastened and folded packaged configuration, the training pant comprising:

a chassis including longitudinal ends, transverse sides, a front region having a pair of transversely opposed front side panels connected to the chassis along front attachment lines and including transverse distal edges defining a transverse width of the training pant at the front region thereof, a back region having a pair of transversely opposed back side panels connected to the chassis along back attachment lines and including transverse distal edges defining a transverse width of the training pant at the back region thereof, a crotch region extending between and interconnecting the front and back regions, first fastening components disposed on the front side panels at or adjacent to each of the distal edges, and corresponding second fastening components disposed on the back side panels at or adjacent to each of the distal edges, in the unfolded and unfastened configuration, the transverse width of the training pant at the front region thereof being substantially equal to the transverse width of the training pant at the back region thereof; and in the pre-fastened and folded packaged configuration, the first fastening components being fastened to the second fastening components to define first and second overlapping refastenable side seams, one of the front side panels and the back side panels being folded twice, once at or near the refastenable side seam and once at or near one of the front attachment lines and the back attachment lines, and the other of said front side panels and the back side panels being folded once at or near one of the front attachment lines and the back attachment lines.

2. The pre-fastened, packaged disposable training pant set forth in claim 1 wherein the back side panel is folded twice and the front side panel is folded once.

3. The pre-fastened, packaged disposable training pant set forth in claim 1 wherein the first and second overlapping refastenable side seams are disposed in overlying relationship with the front region of the training pants in the pre-fastened and folded configuration.

4. A package comprising:
   a flexible packaging bag defining an interior space; and
   a plurality of pre-fastened disposable training pants as set forth in claim 1.

5. The package set forth in claim 4 wherein the flexible packaging bag has a pair of end walls, a pair of side walls, a top wall, and a bottom wall, the walls collectively defining an interior space, the plurality of pre-fastened disposable training pants being compressed within the interior space.

6. The package set forth in claim 5 wherein the plurality of pre-fastened disposable training pants compressed within the interior space exerted an expansion force against the end walls of the flexible packaging bag.

7. The package set forth in claim 4 wherein the flexible packaging bag has a frangible line adapted to be torn to define an opening for accessing the plurality of pre-fastened disposable training pants disposed within the interior space of the flexible packaging bag.

8. The package set forth in claim 4 wherein the flexible packaging bag has a background color of one of blue and pink.

9. The packaging set forth in claim 8 wherein the flexible packaging bag has a printed illustration of at least one of pre-fastened disposable training pants disposed within the interior space of the flexible packaging bag.

\* \* \* \* \*